US007820862B2

(12) United States Patent
Shibasaki et al.

(10) Patent No.: US 7,820,862 B2
(45) Date of Patent: Oct. 26, 2010

(54) LIGAND, METHOD FOR PRODUCING THE SAME, AND CATALYST USING THE LIGAND

(75) Inventors: Masakatsu Shibasaki, Bunkyo-ku (JP); Motomu Kanai, Bunkyo-ku (JP); Ikuo Fujimori, Bunkyo-ku (JP); Kenzo Yamatsugu, Bunkyo-ku (JP); Shin Kamijo, Bunkyo-ku (JP)

(73) Assignee: The University of Tokyo, Tokyo (JP)

( * ) Notice: Subject to any disclaimer, the term of this patent is extended or adjusted under 35 U.S.C. 154(b) by 164 days.

(21) Appl. No.: 12/281,361

(22) PCT Filed: Mar. 2, 2007

(86) PCT No.: PCT/JP2007/054025

§ 371 (c)(1),
(2), (4) Date: Sep. 2, 2008

(87) PCT Pub. No.: WO2007/100086

PCT Pub. Date: Sep. 7, 2007

(65) Prior Publication Data

US 2009/0023579 A1    Jan. 22, 2009

(30) Foreign Application Priority Data

Mar. 3, 2006 (JP) ............................. 2006-057599

(51) Int. Cl.
C07C 9/02 (2006.01)
B01J 31/00 (2006.01)
(52) U.S. Cl. ............................. 568/14; 568/15; 502/158; 502/162; 502/167; 502/171
(58) Field of Classification Search .................. 568/14, 568/15; 502/158, 162, 167, 171
See application file for complete search history.

(56) References Cited

U.S. PATENT DOCUMENTS 6,677,461 B2    1/2004  Shibasaki
2003/0119659 A1  6/2003  Shibasaki

FOREIGN PATENT DOCUMENTS

| JP | 2002-255985 A | 9/2002 |
| JP | 2003-212887 A | 7/2003 |
| JP | 2004-123624 A | 4/2004 |

OTHER PUBLICATIONS

Fujimori, I., et al.,"Key Role of the Lewis Base Position in Asymmetric Bifunctional Catalysis: Design and Evaluation of a New Ligand for Chiral Polymetallic Catalysts," Journal of the American Chemical Society 128(51):16438-16439, 2006.

*Primary Examiner*—Sikarl A Witherspoon
(74) *Attorney, Agent, or Firm*—Christensen O'Connor Johnson Kindness PLLC

(57) ABSTRACT

Disclosed is a novel asymmetric ligand which can be synthesized by a short process at low cost and is capable of exhibiting higher catalytic activity and enantioselectivity than the conventional ligands derived from sugars. Also disclosed are a method for producing such an asymmetric ligand, and a catalyst using such an asymmetric ligand. Specifically disclosed is a ligand represented by the general formula I below or the like. (In the formula, $R^1$ and $R^2$ independently represent 0-5 substituents; X represents P, As or N; m represents an integer of 0-7; n represents an integer of 0-3; $A_1$-$A_4$ independently represent hydrogen, fluorine, chlorine, bromine, benzoyl or acetyl, or alternatively $A_2$ and $A_3$ combine together to form a ring.)

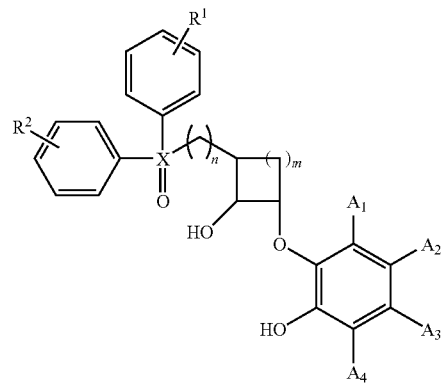

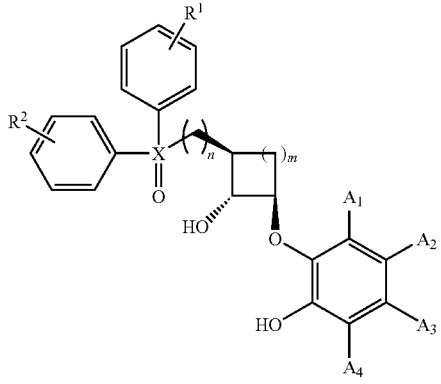

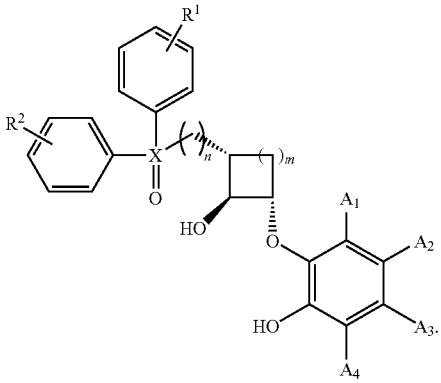

28 Claims, 1 Drawing Sheet

LIGAND, METHOD FOR PRODUCING THE SAME, AND CATALYST USING THE LIGAND

TECHNICAL FIELD

The present invention relates to a novel ligand and a method for producing the ligand, and a catalyst using the ligand.

BACKGROUND ART

The present inventors, or some of the present inventors, or inventors partly including the present inventors have developed a variety of asymmetric ligands having a glucose as a mother nucleus and catalysts therewith (see Patent Document 1 and the like), and have found that the catalysts can promote a variety of catalytically asymmetric reactions such as a catalytically asymmetric cyanation to ketone or ketoimine, a catalytically asymmetric conjugate addition reaction of a cyano group to α,β-unsaturated carboxylic acid derivatives and a catalytically asymmetric ring opening reaction due to a cyano group of aziridine.

Patent Document 1: Japanese Patent No. 3671209

DISCLOSURE OF INVENTION

Problem to be Solved by the Invention

However, since many steps are necessary to synthesize an asymmetric ligand having a glucose as a mother nucleus (hereinafter, in some cases, simply referred to as "glucose-derived ligand"), the ligand was disadvantageous from a standpoint of cost.

Further, it still has a need for catalysts having higher catalytic activity and higher enantioselectivity as well.

An object of the present invention is to provide a novel asymmetric ligand that is synthesized by a short production process at low cost and a producing method thereof, and a catalyst using the novel ligand.

Further, other than or in addition to the above-described objects, an object of the present invention is to provide a novel asymmetric ligand that is capable of developing the catalyst activity and enantioselectivity higher than that of a conventional glucose-derived ligand and a producing method thereof, and a catalyst using the novel ligand.

In particular, an object of the present invention is to provide, in a catalytically asymmetric ring opening reaction in a cyano group of aziridine, which is useful for synthesizing an optically active β-amino acid, a novel asymmetric ligand that is capable of developing functions such as catalyst activity and enantioselectivity excellent more than that of a conventional glucose-derived ligand and a producing method thereof, and a catalyst using the novel ligand.

Means for Solving Problem

The present inventors have found that the following inventions can solve the above-described problems:

<1> A ligand represented by following general formula I:

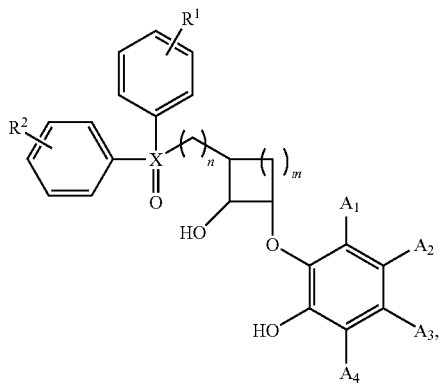

I wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —$OR^a$ ($R^a$ represents a linear or branched alkyl group having 1 to 4 carbon atoms), an amino group represented by —$NR^bR^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$.

<2> A ligand represented by following general formula Ia:

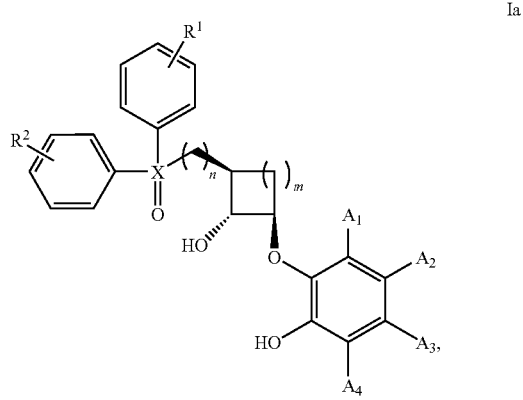

Ia wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —$OR^a$ ($R^a$ represents a linear or branched alkyl group having 1 to 4 carbon atoms), an amino group represented by —$NR^bR^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$.

<3> A ligand represented by following general formula Ib:

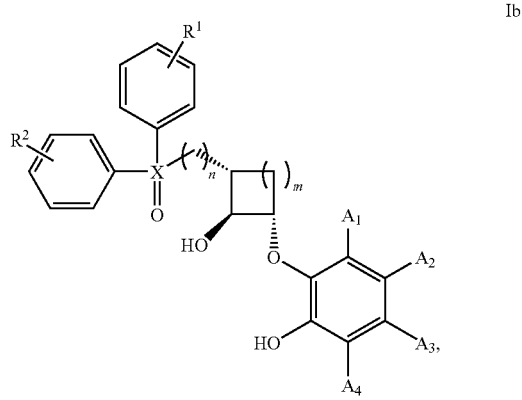

Ib wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —$OR^a$ ($R^a$ represents a linear or branched alkyl group having 1 to 4 carbon atoms), an amino group represented by —$NR^bR^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$.

<4> In any one of the above items <1> to <3>, n may be an integer of 0 or 1, and preferably 0.

<5> In any one of the above items <1> to <4>, m may be an integer of 2 to 4, and preferably 2 or 3.

<6> In any one of the above items <1> to <5>, two of the $A_1$ to $A_4$ may be hydrogen atoms and the other two thereof may be fluorine atoms, preferably $A_1$ and $A_4$ may be hydrogen atoms and $A_2$ and $A_3$ may be fluorine atoms.

<7> A method of producing a ligand represented by following general formula I from a compound represented by following general formula II:

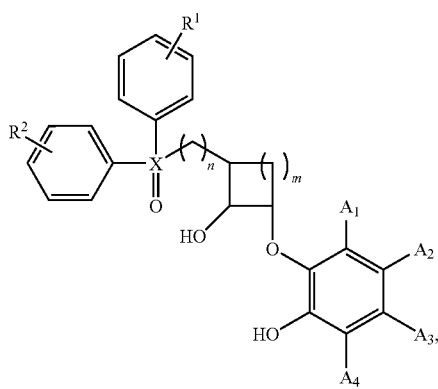

I wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —$OR^a$ ($R^a$ represents a linear or branched alkyl group having 1 to 4 carbon atoms), an amino group represented by —$NR^bR^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$, and

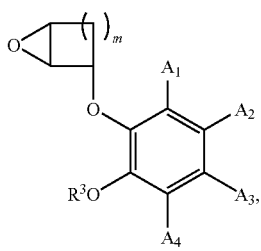

II wherein $R^3$ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of $A_1$ to $A_4$ independently has the same definition as described above, the method comprising the steps of:

a) reacting the compound represented by the general formula II with a metal salt of diphenylphosphine, diarylphosphine or diarylamine;

b) thereafter, processing with ammonium chloride and hydrogen peroxide; and b') when X is As or N and $R^3$ is one other than a hydrogen atom, allowing palladium-carbon to react with hydrogen, lithium chloride, dichlorodicyanobenzoquinone, ceriumammoniumnitrate or a fluorine anion to make the $R^3$ a hydrogen atom, to obtain the ligand represented by the general formula I.

<8> In the above item <7>, the compound represented by the general formula II may be obtained by c) reacting a compound represented by following general formula III, wherein m has the same definition as described above, in the presence of diethylazodicarboxylate or diisopropylazodicarboxylate and triphenylphosphine or tributylphosphine, with a compound represented by following general formula IV, wherein $R^3$ and $A_1$ to $A_4$ have the same definitions as described above:

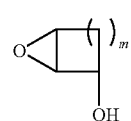

III

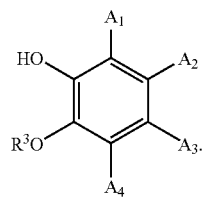

IV

<9> In the above item <8>, the compound represented by the general formula III may be obtained by d) reacting a compound represented by following general formula V, wherein m has the same definition as described above, in the presence of a phosphoric acid buffer, with a peracid:

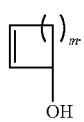

V

<10> A method of producing a ligand represented by following general formula Ia from a compound represented by following general formula IIa:

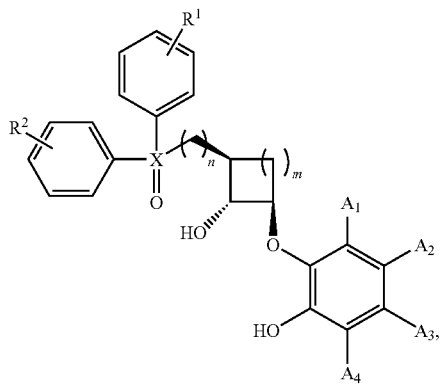

wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —$OR^a$ ($R^a$ represents a linear or branched alkyl group having 1 to 4 carbon atoms), an amino group represented by —$NR^bR^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$, and

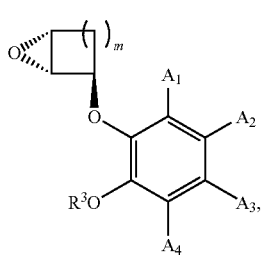

wherein $R^3$ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of $A_1$ to $A_4$ independently has the same definition as described above, the method comprising the steps of:

a) reacting the compound represented by the general formula IIa with a metal salt of diphenylphosphine, diarylphosphine or diarylamine;

b) thereafter, processing with ammonium chloride and hydrogen peroxide; and b') when X is As or N and $R^3$ is one other than a hydrogen atom, allowing palladium-carbon to react with hydrogen, lithium chloride, dichlorodicyanobenzoquinone, ceriumammoniumnitrate or a fluorine anion to make the $R^3$ a hydrogen atom, to obtain the ligand represented by the general formula Ia.

<11> In the above item <10>, the compound represented by the general formula IIa may be obtained by c) reacting a compound represented by following general formula IIIa, wherein m has the same definition as described above, in the presence of diethylazodicarboxylate or diisopropylazodicarboxylate and triphenylphosphine or tributylphosphine, with a compound represented by following general formula IV, wherein $R^3$ and $A_1$ to $A_4$ have the same definitions as described above:

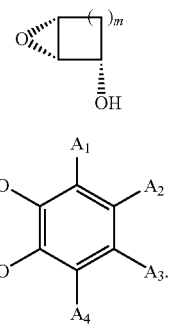

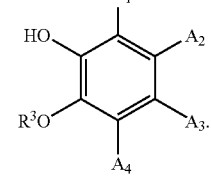

<12> In the above item <11>, the compound represented by the general formula IIIa may be obtained by d) reacting a compound represented by following general formula Va, wherein m has the same definition as described above, in the presence of a phosphoric acid buffer, with a peracid:

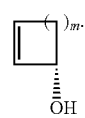

<13> A method of producing a ligand represented by following general formula Ib from a compound represented by following general formula IIb:

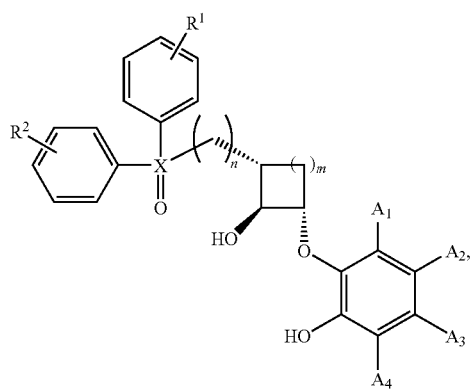

wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —OR$^a$ (R$^a$ represents a linear or branched alkyl group having 1 to 4 carbon atoms), an amino group represented by —NR$^b$R$^c$ (each of R$^b$ and R$^c$ independently represents a hydrogen atom or a linear or branched alkyl group having 1 to 4 carbon atoms), a linear or branched alkyl group having 1 to 4 carbon atoms, a hydroxyl group or a ring formed of A$_2$ and A$_3$, and

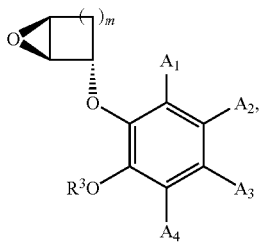

IIb wherein R$^3$ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of A$_1$ to A$_4$ independently has the same definition as described above, the method comprising the steps of:

a) reacting the compound represented by the general formula IIb with a metal salt of diphenylphosphine, diarylphosphine or diarylamine;

b) thereafter, processing with ammonium chloride and hydrogen peroxide; and b') when X is As or N and R$^3$ is one other than a hydrogen atom, allowing palladium-carbon to react with hydrogen, lithium chloride, dichlorodicyanobenzoquinone, ceriumammoniumnitrate or a fluorine anion to make the R$^3$ a hydrogen atom, to obtain the ligand represented by the general formula Ib.

<14> In the above item <13>, the compound represented by the general formula IIb may be obtained by c) reacting a compound represented by following general formula IIIb, wherein m has the same definition as described above, in the presence of diethylazodicarboxylate or diisopropylazodicarboxylate and triphenylphosphine or tributylphosphine, with a compound represented by following general formula IV, wherein R$^3$ and A$_1$ to A$_4$ have the same definitions as described above:

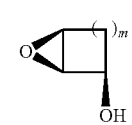

IIIb

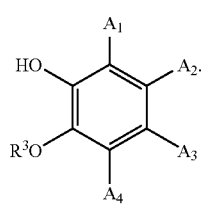

IV

<15> In the above item <14>, the compound represented by the general formula IIIb may be obtained by d) reacting a compound represented by following general formula Vb, wherein m has the same definition as described above, in the presence of a phosphoric acid buffer, with a peracid:

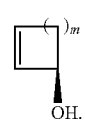

Vb

<16> In any one of the above items <7> to <15>, n may be an integer of 0 or 1, and preferably 0.

<17> In any one of the above items <7> to <16>, m may be an integer of 2 to 4, and preferably 2 or 3.

<18> In any one of the above items <7> to <17>, two of the A$_1$ to A$_4$ may be hydrogen atoms and the other two thereof may be fluorine atoms, preferably A$_1$ and A$_4$ may be hydrogen atoms and A$_2$ and A$_3$ may be fluorine atoms.

<19> In any one of the above items <7> to <18>, R$^3$ may be a methyl group.

<20> A producing method of a ligand represented by following general formula I from a compound represented by following general formula II:

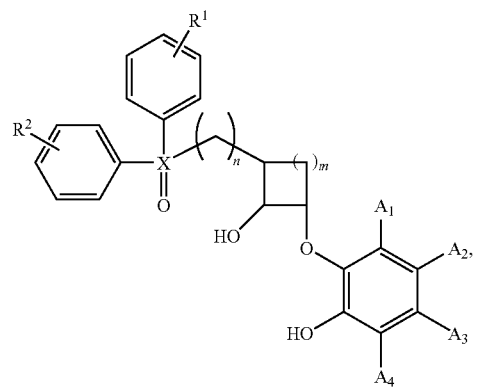

I wherein each of R$^1$ and R$^2$ independently represents 0 to 5 substituent groups; X represents P, As or N; m represents an integer of 0 to 7; n represents an integer of 0 to 3; and each of A$_1$ to A$_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —OR$^a$ (R$^a$ represents a linear or branched alkyl group having 1 to 4 carbon atoms), an amino group represented by —NR$^b$R$^c$ (each of R$^b$ and R$^c$ independently represents a hydrogen atom or a linear or branched alkyl group having 1 to 4 carbon atoms), a linear or branched alkyl group having 1 to 4 carbon atoms, a hydroxyl group or a ring formed of A$_2$ and A$_3$, and

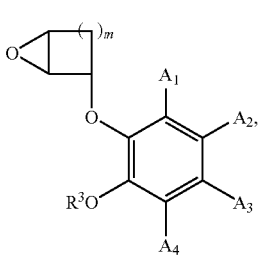

II wherein $R^3$ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of $A_1$ to $A_4$ independently has the same definition as described above, the method comprising the steps of:

g) reacting the compound represented by the general formula II with diethylaluminum cyanide, followed by reacting with concentrated hydrochloric acid, to obtain a compound represented by following general formula VII, wherein m, $R^3$ and $A_1$ to $A_4$ have the same definitions as described above;

h) reacting the compound represented by the general formula VII with a $BH_3$ tetrahydrofuran complex, a $BH_3$ dimethylsulfide complex or $LiAlH_4$, to obtain a compound represented by following general formula VIII, wherein m, $R^3$ and $A_1$ to $A_4$ have the same definitions as described above;

j) reacting the compound represented by the general formula VIII with p-toluenesulfonyl chloride, to obtain a compound represented by following general formula IX, wherein Ts represents a p-toluenesulfonyl group; and m, $R^3$ and $A_1$ to $A_4$ have the same definitions as described above;

k) reacting the compound represented by the general formula IX with potassium diphenyl phosphide, followed by reacting with hydrogen peroxide, to obtain a compound represented by following general formula X, wherein m, $R^3$ and $A_1$ to $A_4$ have the same definitions as described above; and l) reacting the compound represented by the general formula X with lithium iodide, to obtain the ligand represented by the general formula I:

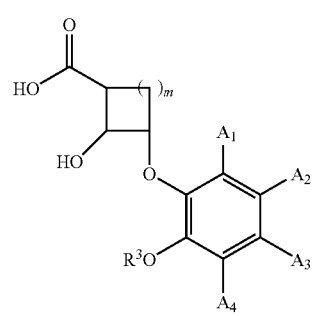

VII

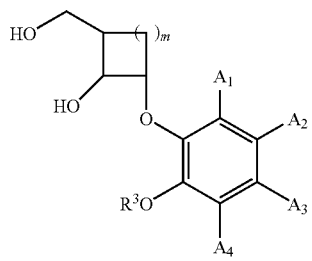

VIII

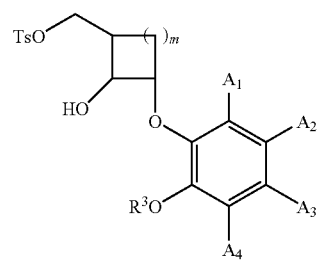

IX

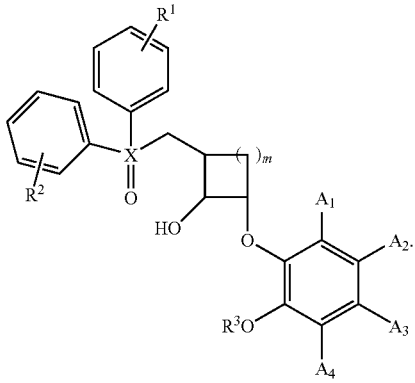

X

<21> A method of producing a ligand represented by following general formula Ia from a compound represented by following general formula IIa:

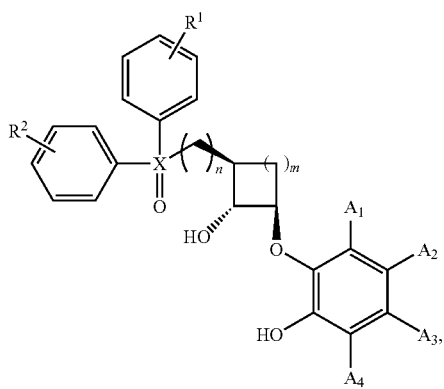

Ia wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by $-OR^a$ ($R^a$ represents a linear or branched alkyl group having 1 to 4 carbon atoms), an amino group represented by $-NR^bR^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$, and

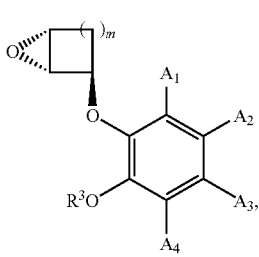

IIa wherein R³ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of $A_1$ to $A_4$ independently has the same definition as described above, the method comprising the steps of:

g) reacting a compound represented by the general formula IIa with diethylaluminum cyanide, followed by reacting with concentrated hydrochloric acid, to obtain a compound represented by following general formula VIIa, wherein m, R³ and $A_1$ to $A_4$ have the same definitions as described above;

h) reacting the compound represented by the general formula VIIa with a BH₃ tetrahydrofuran complex, a BH₃ dimethylsulfide complex or LiAlH₄, to obtain a compound represented by following general formula VIIIa, wherein m, R³ and $A_1$ to $A_4$ have the same definitions as described above;

j) reacting the compound represented by the general formula VIIIa with p-toluenesulfonyl chloride, to obtain a compound represented by following general formula IXa, wherein Ts represents a p-toluenesulfonyl group, and m, R³ and $A_1$ to $A_4$ have the same definitions as described above;

k) reacting the compound represented by the general formula IXa with potassium diphenyl phosphide, followed by reacting with hydrogen peroxide, to obtain a compound represented by following general formula Xa, wherein m, R³ and $A_1$ to $A_4$ have the same definitions as described above; and l) reacting the compound represented by the general formula Xa with lithium iodide, to obtain the ligand represented by the general formula Ia:

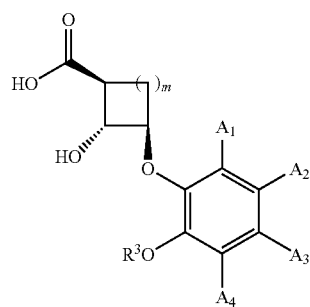

VIIa

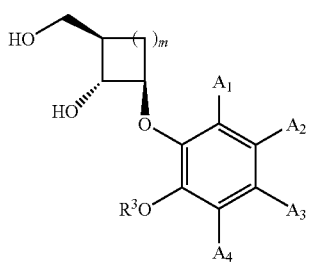

VIIIa

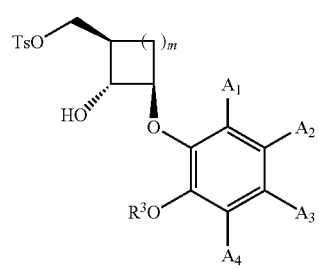

IXa

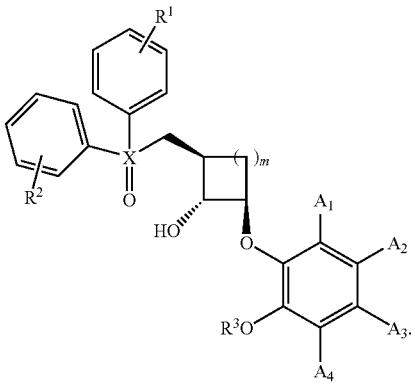

Xa

<22> A method of producing a ligand represented by following general formula Ib from a compound represented by following general formula IIb:

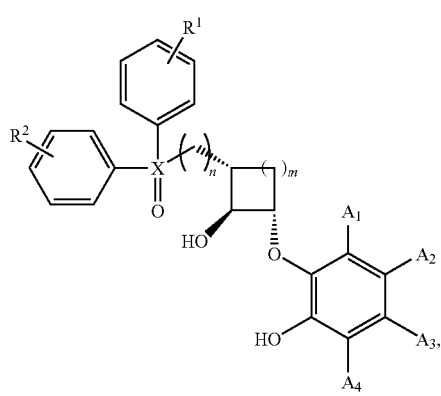

Ib wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —OR$^a$ (R$^a$ represents a linear or branched alkyl group having 1 to 4 carbon atoms), an amino group represented by —NR$^b$R$^c$ (each of R$^b$ and R$^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$, and

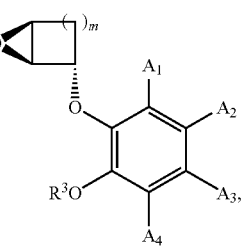

IIb wherein $R^3$ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of $A_1$ to $A_4$ independently has the same definition as described above, the method comprising the steps of:

g) reacting a compound represented by the general formula IIb with diethylaluminum cyanide, followed by reacting with concentrated hydrochloric acid, to obtain a compound represented by following general formula VIIb, wherein m, $R^3$ and $A_1$ to $A_4$ have the same definitions as described above;

h) reacting the compound represented by the general formula VIIb with a $BH_3$ tetrahydrofuran complex, a $BH_3$ dimethylsulfide complex or $LiAlH_4$, to obtain a compound represented by following general formula VIIIb, wherein m, R and $A_1$ to $A_4$ have the same definitions as described above;

j) reacting the compound represented by the general formula VIIIb with p-toluenesulfonyl chloride, to obtain a compound represented by following general formula IXb, wherein Ts represents a p-toluenesulfonyl group, and m, $R^3$ and $A_1$ to $A_4$ have the same definitions as described above;

k) reacting the compound represented by the general formula IXb with potassium diphenyl phosphide, followed by reacting with hydrogen peroxide, to obtain a compound represented by following general formula Xb, wherein m, $R^3$ and $A_1$ to $A_4$ have the same definitions as described above; and l) reacting the compound represented by the general formula Xb with lithium iodide, to obtain the ligand represented by the general formula Ib:

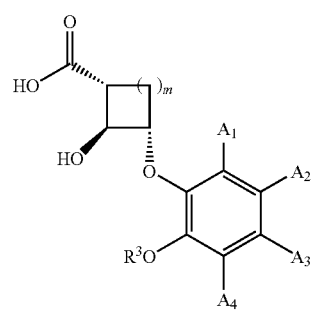

VIIb

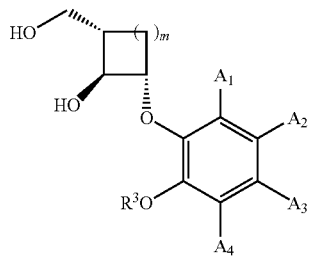

VIIIb

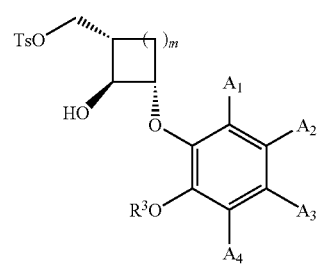

IXb

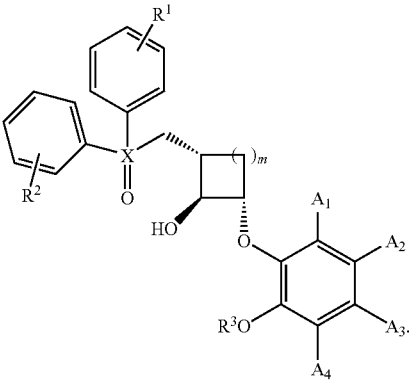

Xb

<23> In any one of the above items <20> to <22>, n may be an integer of 0 or 1, and preferably 0.

<24> In any one of the above items <20> to <23>, m may be an integer of 2 to 4, and preferably 2 or 3.

<25> In any one of the above items <20> to <24>, two of the $A_1$ to $A_4$ may be hydrogen atoms and the other two thereof may be fluorine atoms, preferably $A_1$ and $A_4$ may be hydrogen atoms and $A_2$ and $A_3$ may be fluorine atoms.

<26> In any one of the above items <20> to <25>, $R^3$ may be a methyl group.

<27> A catalyst being formed of:

A) a metal alkoxide or a metal amide represented by $M_x(OR^4)_y$ or $M_{x'}(NR^5)_{y'}$, wherein M is a metal selected from the group consisting of titanium, zirconium, aluminum, gallium, barium and rare earth elements; each of $R^4$ and $R^5$ independently represents a substituted or non-substituted, linear or branched or cyclic alkyl group having 2 to 6 carbon atoms, a substituted or non-substituted, linear or branched or cyclic alkenyl group, a substituted or non-substituted aromatic group or a trialkylsilyl group, and x and y and x' and y' are integers stoichiometrically determined by the metal M; and B) a ligand represented by following general formula I, wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by $—OR^a$ ($R^a$ represents a linear or branched alkyl group having 1 to 4 carbon atoms), an amino group represented by $—NR^bR^c$ (each of $R^b$ and $R^c$ independently represents a hydrogen atom, or a linear or branched alkyl group having 1 to 4 carbon atoms), a linear or branched alkyl group having 1 to 4 carbon atoms, a hydroxyl group or a ring formed of $A_2$ and $A_3$:

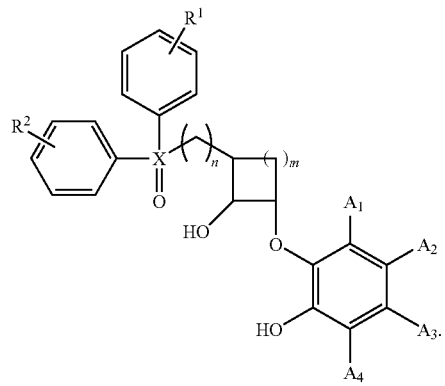

I

<28> In the above item <27>, the B) ligand may be represented by following general formula Ia:

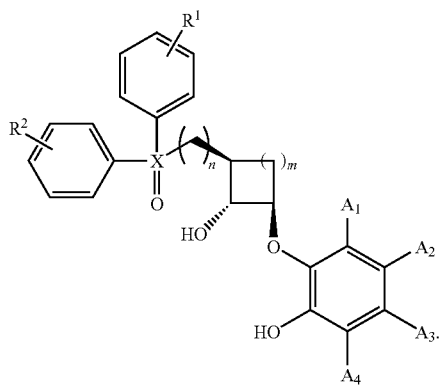

<29> In the above item <27>, the B) ligand may be represented by following general formula Ib:

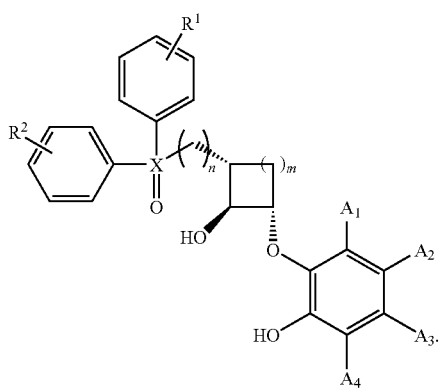

<30> In any one of the above items <27> to <29>, the A) metal alkoxide or metal amide and B) ligand may be 1:1 to 1:4 by molar ratio of A:B.

<31> In any one of the above items <27> to <30>, the rare earth metal may be ytterbium, yttrium, lanthanum, cerium, praseodymium, samarium, europium, gadolinium, dysprosium, holmium or erbium.

<32> In any one of the above items <27> to <31>, an alkyl group of the trialkylsilyl group may be a linear or branched alkyl having 1 to 4 carbon atoms.

<33> In any one of the above items <27> to <32>, the A) metal alkoxide or metal amide may be gadolinium triisopropoxide, yttrium triisopropoxide, tris-[N,N-bis(trimethylsilyl)amide]gadolinium (III), tris-[N,N-bis(trimethylsilyl)amide]yttrium (III) or barium diisopropoxide.

<34> In any one of the above items <27> to <33>, n may be an integer of 0 or 1, and preferably 0.

<35> In any one of the above items <27> to <34>, m may be an integer of 2 to 4, and preferably 2 or 3.

<36> In any one of the above items <27> to <35>, two of the $A_1$ to $A_4$ may be hydrogen atoms and the other two thereof may be fluorine atoms, preferably $A_1$ and $A_4$ may be hydrogen atoms and $A_2$ and $A_3$ may be fluorine atoms.

<C1> A ligand represented by the above-described general formula Ia, wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, or a ring formed of $A_2$ and $A_3$.

<C2> In the above item <C1>, n may be an integer of 0 or 1, and preferably 0.

<C3> In the above item <C1> or <C2>, m may be an integer of 2 to 4, and preferably 2 or 3.

<C4> In any one of the above items <C1> to <C3>, two of the $A_1$ to $A_4$ may be hydrogen atoms and the other two thereof may be fluorine atoms, preferably $A_1$ and $A_4$ may be hydrogen atoms and $A_2$ and $A_3$ may be fluorine atoms.

<C5> A method of producing a ligand represented by the above-described general formula Ia (wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, or a ring formed of $A_2$ and $A_3$) from a compound represented by the above-described general formula IIa (wherein $R^3$ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of $A_1$ to $A_4$ independently has the same definition as described above);
the method comprising the steps of:

a) reacting the compound represented by the general formula IIa with a metal salt of diphenylphosphine, diarylphosphine or diarylamine;

b) thereafter, processing with ammonium chloride and hydrogen peroxide; and b') when X is As or N and $R^3$ is one other than a hydrogen atom, allowing palladium-carbon to react with hydrogen, lithium chloride, dichlorodicyanobenzoquinone, ceriumammoniumnitrate or a fluorine anion (for example, a fluorine anion derived from tetrabutylammonium fluoride) to make the $R^3$ a hydrogen atom, to obtain the ligand represented by the general formula Ia.

<C6> In the above item <C5>, the compound represented by the general formula IIa may be obtained by c) reacting a compound represented by the above-described general formula IIIa, wherein m has the same definition as described above, in the presence of diethylazodicarboxylate or diisopropylazodicarboxylate and triphenylphosphine or tributylphosphine, with a compound represented by the above-described general formula IV, wherein $R^3$ and $A_1$ to $A_4$ have the same definitions as described above.

<C7> In the above item <C6>, the compound represented by the general formula IIIa may be obtained by d) reacting a compound represented by the above-described general formula Va, wherein m has the same definition as described above, in the presence of a phosphoric acid buffer, with a peracid (such as 3-chloroperbenzoic acid, perbenzoic acid, peracetic acid or hydrogen peroxide, in particular, 3-chloroperbenzoic acid being preferred).

<C8> In any one of the above items <C5> to <C7>, n may be an integer of 0 or 1, and preferably 0.

<C9> In any one of the above items <C5> to <C8>, m may be an integer of 2 to 4, and preferably 2 or 3.

<C10> In any one of the above items <C5> to <C9>, two of the $A_1$ to $A_4$ may be hydrogen atoms and the other two thereof may be fluorine atoms, preferably $A_1$ and $A_4$ may be hydrogen atoms and $A_2$ and $A_3$ may be fluorine atoms.

<C11> In any one of the above items <C5> to <C9>, $R^3$ may be a methyl group.

<C12> A method of producing a ligand represented by the above-described general formula Ia (wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, or a ring formed of $A_2$ and $A_3$) from a compound represented by the above-described general formula IIa (wherein $R^3$ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of $A_1$ to $A_4$ independently has the same definition as described above);

the method comprising the steps of:

g) reacting a compound represented by the general formula IIa with diethylaluminum cyanide, followed by reacting with concentrated hydrochloric acid, to obtain a compound represented by the above-described general formula VIIa, wherein m, $R^3$ and $A_1$ to $A_4$ have the same definitions as described above;

h) reacting the compound represented by the general formula VIIa with $BH_3$, to obtain a compound represented by the above-described general formula VIIIa, wherein m, $R^3$ and $A_1$ to $A_4$ have the same definitions as described above;

j) reacting the compound represented by the general formula VIIIa with p-toluenesulfonyl chloride, to obtain a compound represented by following general formula IXa, wherein Ts represents a p-toluenesulfonyl group, and m, $R^3$ and $A_1$ to $A_4$ have the same definitions as described above;

k) reacting the compound represented by the general formula IXa with potassium diphenyl phosphide, followed by reacting with hydrogen peroxide, to obtain a compound represented by the above-described general formula Xa, wherein m, $R^3$ and $A_1$ to $A_4$ have the same definitions as described above; and l) reacting the compound represented by the general formula Xa with lithium iodide, to obtain the ligand represented by the general formula Ia.

<C13> In the above item <C12>, n may be an integer of 0 or 1, and preferably 0.

<C14> In the above item <C12> or <C13>, m may be an integer of 2 to 4, and preferably 2 or 3.

<C15> In any one of the above items <C12> to <C14>, two of the $A_1$ to $A_4$ may be hydrogen atoms and the other two thereof may be fluorine atoms, preferably $A_1$ and $A_4$ may be hydrogen atoms and $A_2$ and $A_3$ may be fluorine atoms.

<C16> In any one of the above items <C12> to <C15>, $R^3$ may be a methyl group.

<C17> A catalyst being formed of:

A) a metal alkoxide or a metal amide represented by $M_x(OR^4)_y$ or $M_x(NR^5)_{y'}$, wherein M is a metal selected from the group consisting of titanium, zirconium, aluminum, gallium and rare earth elements; each of $R^4$ and $R^5$ independently represents a substituted or non-substituted, linear or branched or cyclic alkyl group having 2 to 6 carbon atoms, a substituted or non-substituted, linear or branched or cyclic alkenyl group, a substituted or non-substituted aromatic group or a trialkylsilyl group, and x and y and x' and y' are integers stoichiometrically determined by the metal M; and B) a ligand represented by the above-described general formula Ia, wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group or a ring formed of $A_2$ and $A_3$.

<C18> In the above item <C17>, the A) metal alkoxide or metal amide and B) ligand may be 1:1 to 1:4 by molar ratio of A:B.

<C19> In the above item <C17> or <C18>, the rare earth metal may be ytterbium, yttrium, lanthanum, cerium, praseodymium, samarium, europium, gadolinium, dysprosium, holmium or erbium.

<C20> In any one of the above items <C17> to <C19>, an alkyl group of the trialkylsilyl group may be a linear or branched alkyl having 1 to 4 carbon atoms.

<C21> In any one of the above items <C17> to <C20>, the A) metal alkoxide or metal amide may be gadolinium triisopropoxide, yttrium triisopropoxide, tris-[N,N-bis(trimethylsilyl)amide]gadolinium (III), or tris-[N,N-bis(trimethylsilyl)amide]yttrium (III).

<C22> In any one of the above items <C17> to <C21>, n may be an integer of 0 or 1, and preferably 0.

<C23> In any one of the above items <C17> to <C22>, m may be an integer of 2 to 4, and preferably 2 or 3.

<C24> In any one of the above items <C17> to <C23>, two of the $A_1$ to $A_4$ may be hydrogen atoms and the other two thereof may be fluorine atoms, preferably $A_1$ and $A_4$ may be hydrogen atoms and $A_2$ and $A_3$ may be fluorine atoms.

EFFECTS OF THE INVENTION

The present invention can provide a novel asymmetric ligand that is synthesized by a short production process at low cost and a producing method thereof, and a catalyst using the novel ligand.

Further, other than or in addition to the above-described effects, the present invention can provide a novel asymmetric ligand that is capable of developing the catalyst activity and enantioselectivity higher than that of a conventional glucose-derived ligand and a producing method thereof, and a catalyst using the novel ligand.

In particular, the present invention can provide, in a catalytically asymmetric ring opening reaction in a cyano group of aziridine, which is useful for synthesizing an optically active β-amino acid, a novel asymmetric ligand that is capable of developing functions such as catalyst activity and enantioselectivity excellent more than that of a conventional glucose-derived ligand and a producing method thereof, and a catalyst using the novel ligand.

BEST MODE FOR CARRYING OUT THE PRESENT INVENTION

The present invention will be described in detail hereinafter.

The present invention provides a novel asymmetric ligand.

<Asymmetric Ligand>

A ligand according to the present invention may be represented by a formula I or Ia or Ib shown below (hereinafter, in some cases, formulas I, Ia and Ib are abbreviated as "formula I or the like"). In the formulas, each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by $-OR^a$ ($R^a$ represents a linear or branched alkyl group having 1 to 4 carbon atoms), an amino group represented by $NR^bR^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$.

As can be seen from the formula I or the like, the ligand according to the present invention is different from a conventional ligand of which mother nucleus is derived from glucose (such as Japanese Patent No. 3671209). The ligand according to the present invention, which is different in a structure from that of a conventional ligand, has a function such as described below. For instance, according to the ligand of the present invention, a catalyst using the ligand has high catalyst activity and/or high enantioselectivity.

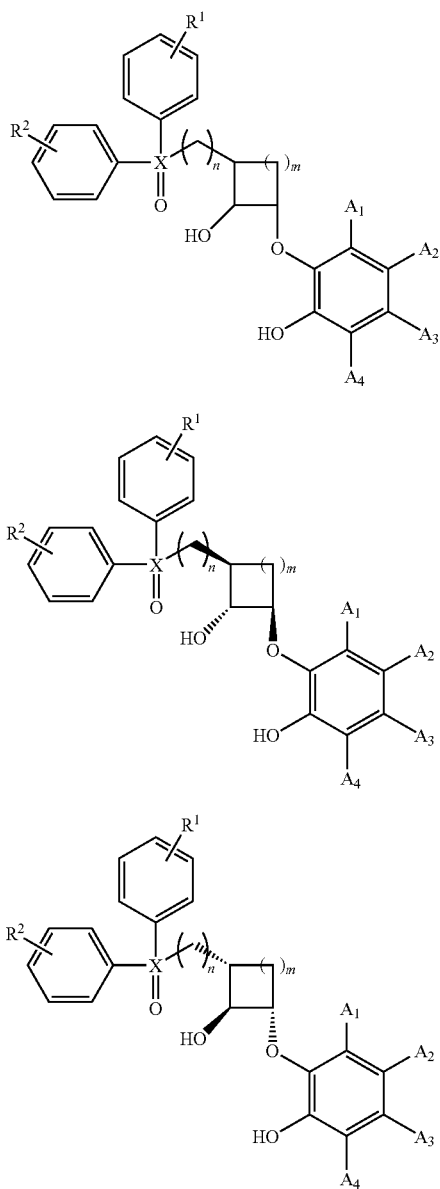

In the formulas, n may be an integer of 0 or 1, preferably 0; m may be an integer of 2 to 4 and preferably 2 or 3; and X may be P or N, preferably P.

Among $A_1$ to $A_4$, preferably two may be hydrogen atoms, and the other two may be fluorine atoms, and more preferably $A_1$ and $A_4$ may be hydrogen atoms and $A_2$ and $A_3$ may be fluorine atoms.

<Method of Preparing Asymmetric Ligand>

An asymmetric ligand according to the present invention may be prepared:

From a compound represented by the formulas II or the like (the phrase "the formula II or the like" used herein means a formula II, IIa or IIb, and, hereinafter, in some cases, simply abbreviated as "formula II or the like"), a ligand represented by the formula I or the like may be prepared. The method comprises the step of:

a) reacting a compound represented by the formula II or the like with a metal salt of diphenylphosphine, a metal salt of diarylphosphine or a metal salt of diarylamine;

b) thereafter processing with ammonium chloride and hydrogen peroxide; and b') when X is As or N and $R^3$ is other than a hydrogen atom, allowing palladium-carbon to react with hydrogen, lithium chloride, dichlorodicyanobenzoquinone, ceriumammoniumnitrate or a fluorine anion (such as fluorine anion derived from tetrabutylammonium fluoride) to make $R^3$ a hydrogen atom.

Herein, in the formula II or the like, $R^3$ represents a hydrogen atom, a linear or branched alkyl group having 1 to 8 carbon atoms, a linear or branched alkenyl group having 2 to 8 carbon atoms, a benzyl group, a paramethoxybenzyl group or a silyl group. $R^3$ preferably represents a methyl group or a benzyl group and more preferably a methyl group. In the formula II or the like, m and $A_1$ to $A_4$ have same definitions as described above.

The step a), depending on compounds used, may be carried out by use of a solvent such as tetrahydrofuran (hereinafter, abbreviated as "THF"), ethers or dioxane under conditions of −78 to 50° C.

Further, the step b), depending on compounds used, may be carried out by use of a solvent such as THF, ethers or dioxane under conditions of −20 to 20° C.

More, the step b'), depending on compounds used, may be carried out by use of a solvent such as THF, ethers, dioxane, methylene chloride, dimethyl formamide, or dimethyl sulfoxide under conditions of −78 to 50° C.

The producing method that has the steps a) and b) (and step b')) is preferred when one where n is zero in the formula I is obtained and in less steps.

Further, a compound represented by the formula II or the like is prepared as follows:

c) Reacting a compound represented by the formula III or the like (Herein, "the formula III or the like" means formula III, IIIa or IIIb. Hereinafter, in some cases, these are simply abbreviated to as "formula III or the like"), under the presence of diethylazodicarboxylate or diisopropylazodicarboxylate and triphenyl phosphine or tributyl phosphine, preferably under the presence of diisopropylazodicarboxylate, with a compound represented by the formula IV can obtain a compound represented by the formula II or the like. In the formula III or the like and IV, m, $R^3$ and $A_1$ to $A_4$ have the same definitions as described above.

The step c), depending on compounds used, may be carried out by use of a solvent such as THF, ethers, or dioxane under conditions of 0 to 50° C.

Further, a compound represented by the formula III or the like is prepared as follows:

d) Reacting a compound represented by the formula V or the like (Herein, "the formula V or the like" means formulas V, Va or Vb. Hereinafter, in some cases, these are simply abbreviated as "formula V or the like"), under the presence of a phosphoric acid buffer, with a peracid (such as 3-chloroperbenzoic acid, perbenzoic acid, peracetic acid or hydrogen peroxide, 3-chloroperbenzoic acid being particularly preferred) can obtain a compound represented by the formula III or the like. In the formula V or the like, m has the same definition as described above.

The step d), depending on compounds used, may be carried out by use of a solvent such as methylene chloride, chloroform, ethers or dioxane under conditions of −20 to 20° C.

More, a ligand according to the present invention may be produced from a compound represented by the formula II or the like through a route different from the above-mentioned ones.

The method may comprise the steps of:

g) reacting the compound represented by the general formula II or the like with diethylaluminum cyanide, followed by reacting with concentrated hydrochloric acid, to obtain a compound represented by the formula VII or the like (the term "the formula VII or the like" used herein means a formula VII, VIIa or VIIb. Hereinafter, in some cases, these are simply abbreviated as "the formula VII or the like");

h) reacting the compound represented by the general formula VII or the like with a BH$_3$ tetrahydrofuran complex, a BH$_3$ dimethylsulfide complex or LiAlH$_4$, to obtain a compound represented by the formula VIII or the like (the term "the formula VIII or the like" used herein means a formula VIII, VIIIa or VIIIb. Hereinafter, in some cases, these are simply abbreviated as "the formula VIII or the like");

j) reacting the compound represented by the formula VIII or the like with p-toluenesulfonyl chloride, to obtain a compound represented by the formula IX or the like (the term "the formula IX or the like" used herein means a formula IX, IX a or IX b. Hereinafter, in some cases, these are simply abbreviated as "the formula IX or the like");

k) reacting the compound represented by the formula IX or the like with potassium diphenyl phosphide, followed by reacting with hydrogen peroxide, to obtain a compound represented by the formula X or the like (the term "the formula X or the like" used herein means a formula X, X a or X b. Hereinafter, in some cases, these are simply abbreviated as "the formula X or the like"); and l) reacting the compound represented by the general formula X with lithium iodide, to obtain the ligand represented by the formula I or the like.

In the formulae VII or the like, VIII or the like, TX or the like and X or the like, m, R$^3$ and A$_1$ to A$_4$ have the same definitions as described above. Further, in the formula IX or the like, Ts represents p-toluenesulfonyl group.

The step g), depending on compounds used, may be carried out by use of a solvent such as THF, ethers, dioxane or toluene under conditions of −20 to 100° C.

The step h), depending on compounds used, may be carried out by use of a solvent such as THF, ethers, dioxane or toluene under conditions of −20 to 20° C.

The step j), depending on compounds used, may be carried out by use of a solvent such as methylene chloride or pyridine under conditions of −78 to 50° C.

The step k), depending on compounds used, may be carried out by use of a solvent such as THF, ethers, dioxane or toluene under conditions of −78 to 50° C.

The step l), depending on compounds used, may be carried out by use of a solvent such as dimethyl formamide or dimethyl sulfoxide under conditions of −78 to 200° C.

<Catalyst>

The present invention provides a catalyst using the above-described asymmetric ligand.

A catalyst according to the present invention is formed of a metal alkoxide or a metal amide represented by A) M$_x$(OR$^4$)$_y$, or M$_{x'}$(NR$^5$)$_{y'}$; and B) a ligand represented by the formula I.

Herein, M is a metal selected from a group of titanium, zirconium, aluminum, gallium, barium and rare earth elements. Each of R$^4$ and R$^5$ independently represents a substituted or non-substituted linear or branched or cyclic alkyl group having 2 to 6 carbon atoms, a substituted or non-substituted linear or branched or cyclic alkenyl group, a substituted or non-substituted aromatic group or a trialkylsilyl group, wherein x and y and x' and y' are integers determined stoichiometrically by the metal M. An alkyl group of the trialkylsilyl group may be a linear or branched alkyl having 1 to 4 carbon atoms.

Among the M, preferable examples of the rare earth metals may include ytterbium, yttrium, lanthanum, cerium, praseodymium, samarium, europium, gadolinium, dysprosium, holmium and erbium. The M is particularly preferably gadolinium or yttrium.

Preferable examples of A) metal alkoxides or metal amides may include gadolinium triisopropoxide, yttrium triisopropoxide, tris-[N,N-bis(trimethylsilyl)amide]gadolinium (III) and tris-[N,N-bis(trimethylsilyl)amide]yttrium (III).

Furthermore, A) metal alkoxide or metal amide is preferably barium diisopropoxide.

Herein, "being formed of" means a state including all of i) a case where both of the A component and B component work as a catalyst, ii) a case where OR$^4$ or OR$^5$ of the A component is partially or entirely substituted by a ligand of the B component to work as a catalyst, and iii) a case where both states of the i) and ii) are present and work as a catalyst.

In the A) metal alkoxide or metal amide and B) ligand, a mole ratio of A:B is 1:1 to 1:4 and preferably 1:1 to 1:2.

Such a catalyst may be prepared as shown below: Mixing the A component and B component in THF or propionitrile such that the mixture is in the above-described mole ratio, followed by reacting the mixture at a temperature from room temperature to 80° C. can obtain the catalyst.

The present invention will be illustrated in more detail by way of, but is not limited to the following examples. Furthermore, FIG. 1 shows a scheme surveying following examples.

EXAMPLE 1

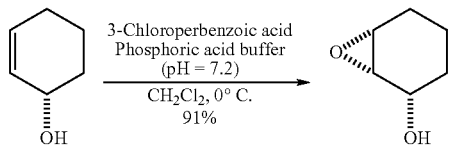

Optically active allylalcohol (see Lussem, B. J.; Gais, H.-J. J. Am. Chem. Soc. 2003, 125, 6066, 100 mg, 0.968 mmol) was dissolved in methylene chloride (10 mL) and a phosphoric acid buffer (2 mL), followed by, under ice-cooling, adding 3-chloroperbenzoic acid (0.34 g, 0.968 mmol). After stirring for 1 hr, sodium sulfate was added and a reaction solution was purified directly by means of alumina column chromatography (eluting solvent=methylene chloride→ethyl acetate) to obtain a target subject, epoxy alcohol (0.34 g, yield: 91%).

NMR (CDCL₃) δ 1.21-1.31 (1H, m), 1.41-1.49 (1H, m), 1.51-1.60 (2H, m), 1.75-1.81 (1H, m), 1.84-1.90 (1H, m), 1.98 (1H, brs), 3.31 (1H, t, J=3.7 Hz), 3.34 (1H, t, J=3.7 Hz), 4.00 (1H, brs).

EXAMPLE 2

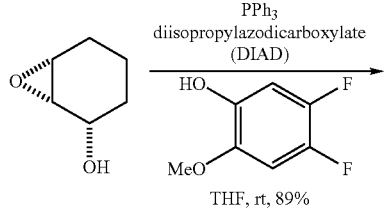

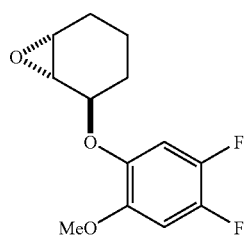

To a solution of triphenyl phosphine (1.12 g, 4.27 mmol) and monomethylfluorocatecol (684 mg, 4.27 mmol) in tetrahydrofuran (hereinafter, simply abbreviated as "THF") (5 mL), a solution (1 mL) of diisopropylazodicarboxylate (DIAD) (840 mL, 4.27 mmol) and epoxy alcohol (325 mg, 2.85 mmol) in THF was added under ice-cooling. After reacting the mixture at room temperature for 18 hr, the mixture was diluted with ethyl acetate, followed by washing an organic layer with water and a saturated saline solution. The organic layer was dried over sodium sulfate, filtered and concentrated. A resulting crude product was purified by use of silica gel column chromatography (ethyl acetate:hexane=1:5), thereby to obtain a target product, epoxy ether (649 mg, yield: 89%).

NMR (CDCL₃) δ 1.24-1.33 (1H, m), 1.40-1.48 (1H, m), 1.51-1.57 (1H, m), 1.78-1.85 (1H, m), 1.89-1.95 (1H, m), 2.04-2.10 (1H, m), 3.22 (1H, d, J=3.5 Hz), 3.26-3.28 (1H, m), 4.36 (1H, dd, J=9.0, 5.5 Hz), 6.73 (1H, dd, J=12, 7.7 Hz), 6.86 (1H, dd, J=12, 7.7 Hz).

EXAMPLE 3

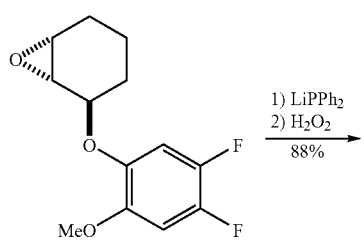

-continued

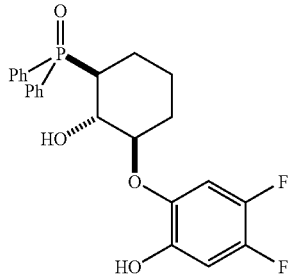

Epoxy ether (1.50 g, 5.85 mmol) was dissolved in THF (20 mL), followed by adding diphenyl phosphine (3 mL, 17.6 mmol) and BuLi (1.6 M in hexane, 10 mL, 17.6 mmol) at −78° C. to react the mixture for 20 min. Thereafter, after stirring at room temperature for 15 hr, a saturated ammonium chloride aqueous solution was added. The resulting solution was ice-cooled, followed by adding hydrogen peroxide water (5 mL) and stirring for 30 min, further followed by adding a saturated sodium thiosulfate aqueous solution. A resulting product was extracted with ethyl acetate, followed by washing an organic layer with a saturated saline solution. The organic layer was dried over sodium sulfate, followed by filtering and concentrating. A resulting product was subjected to silica gel column chromatography (ethyl acetate:hexane=1:1→2:1) to obtain a target subject, phosphine oxide (2.29 g, yield: 88%). The resulting crystal was recrystallized from isopropyl alcohol to obtain an asymmetric ligand having 100% optical purity. The optical purity of the ligand was confirmed by use of the optically active HPLC (trade name: CHIRALCEL-ODH, produced by Daicel, isopropyl alcohol: hexane=1:9, flow rate: 1.0 mL/min, $t_R$=6.8 min (minor: not observed), 9.5 min (major)).

NMR (CDCL₃) δ 1.0-1.1 (1H, m), 1.30-1.38 (1H, m), 1.40-1.50 (1H, m), 1.68-1.83 (2H, m), 2.15-2.22 (1H, m), 2.66 (1H, m), 3.58-3.63 (1H, m), 3.98-4.04 (1H, m), 3.58-3.64 (1H, m), 3.98-4.04 (1H, m), 6.73-6.79 (2H, m), 6.88 (1H, brs), 7.50-7.57 (4H, m), 7.58-7.66 (2H, m), 7.71-7.78 (4H, m).

EXAMPLE 4

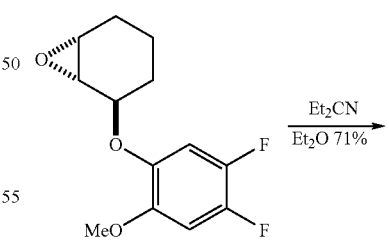

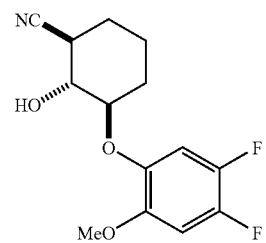

Epoxy ether (100 mg, 0.390 mmol) was dissolved in diethyl ether (3.9 mL), followed by adding diethyl aluminum cyanide (1.0 M in toluene, 470 mL, 0.585 mmol) at 0° C. to react the mixture for 3 hr, further followed by adding a saturated sodium chloride aqueous solution. Thereto, a saturated Rochelle salt aqueous solution was added, followed by stirring for 1 hr. A product was extracted with ethyl acetate and an organic layer was washed with a saturated saline solution. The organic layer was dried over sodium sulfate, followed by filtering and concentrating, further followed by subjecting a resulting product to silica gel column chromatography (ethyl acetate:hexane=5:2), thereby to obtain a target object, cyanohydrin (80 mg, yield: 73%).

NMR (CDCL$_3$) δ1.24-1.34 (1H, m), 1.48-1.56 (1H, m), 1.64 (1H, m), 1.82-1.88 (1H, m), 2.07-2.18 (2H, m), 2.50 (1H, ddd, J=13, 10, 3.7 Hz), 3.78-3.82 (1H, m), 3.83 (3H, s), 4.02 (1H, brs), 6.75 (1H, dd, J=12, 7.6 Hz), 6.85 (1H, dd, J=12, 7.6 Hz).

EXAMPLE 5

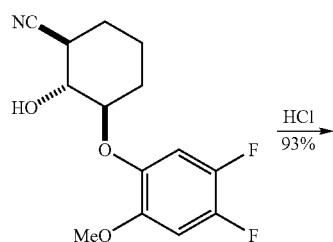

Cyanohydrin (196 mg, 0.691 mmol) was dissolved in dimethoxy ethane (15 mL), followed by adding 12N hydrochloric acid (15 mL) and reacting the mixture at 85° C. for 24 hr. A resulting product was extracted with ethyl acetate, followed by washing an organic layer with a saturated saline solution. The organic layer was dried over sodium sulfate, filtered and concentrated. A resulting product was dissolved in 3N sodium hydroxide aqueous solution (1 mL), followed by washing with diethyl ether. To a resulting product, 1N hydrochloric acid was added, followed by extracting with ethyl acetate, an organic layer was dried over sodium sulfate, filtered and concentrated, thereby to obtain a target subject, hydroxycarboxylic acid (374 mg, yield: quant).

NMR (CDCL$_3$) δ 1.28-1.37 (1H, m), 1.46-1.60 (1H, m), 1.84-1.90 (1H, m), 2.08-2.14 (1H, m), 2.15-2.21 (1H, m), 2.43 (1H, ddd, J=12.5, 10.5, 4.3 Hz), 3.68 (1H, ddd, J=11.3, 8.6, 4.9 Hz), 3.85 (3H, s), 3.93 (1H, dd, J=10.7, 8.9 Hz), 6.76 (1H, dd, J=11.3, 7.7 Hz), 6.89 (1H, dd, J=10.7, 7.9 Hz).

EXAMPLE 6

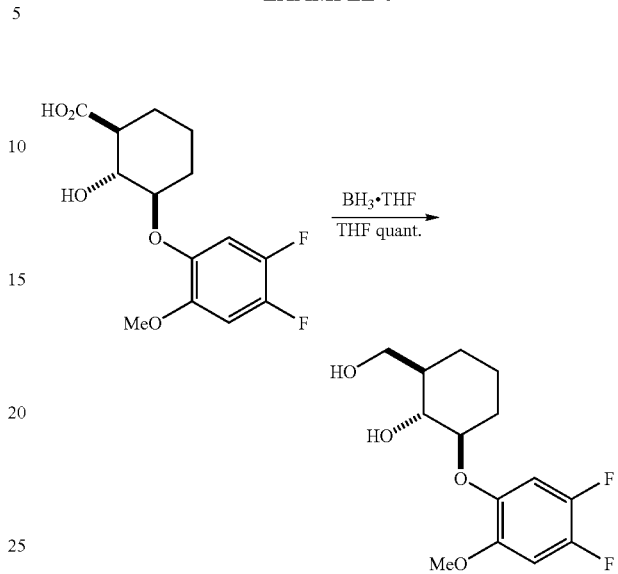

Hydroxycarboxylic acid (295 mg, 0.976 mmol) was dissolved in THF (5 mL), followed by adding borane tetrahydrofuran complex (1.17 M in THF, 3.34 mL, 3.90 mmol) to react the mixture for 2 hr. Thereafter, 1N hydrochloric acid was added, followed by adding a saturated sodium hydrogen carbonate aqueous solution. A product was extracted with ethyl acetate, followed by washing an organic layer with a saturated saline solution, further followed by drying over sodium sulfate, filtering and concentrating. A resulting product was subjected to silica gel column chromatography (ethyl acetate:hexane=2:3), thereby to obtain a target object, diol (281 mg, yield: quant). The resulting crystal was recrystallized from methylene chloride and hexane to obtain diol having 100% optical purity. The optical purity of the diol body was confirmed by use of the optically active HPLC (trade name: CHIRALCEL-ADH, produced by Daicel, isopropyl alcohol:hexane=1:9, flow rate: 1.0 mL/min, t$_R$=12.2 min (major), 14.9 min (minor: not observed)).

NMR (CDCL$_3$) δ 1.05 (1H, ddd, J=26.3, 13.1, 3.7 Hz), 1.28-1.38 (1H, m), 1.42-1.51 (1H, m), 1.60-1.74 (2H, m), 1.77-1.82 (1H, m), 2.11-2.17 (1H, m), 3.62-3.75 (4H, m), 3.84 (3H, s), 3.91 (1H, brs), 6.74 (1H, dd, J=11.0, 8.0 Hz).

EXAMPLE 7

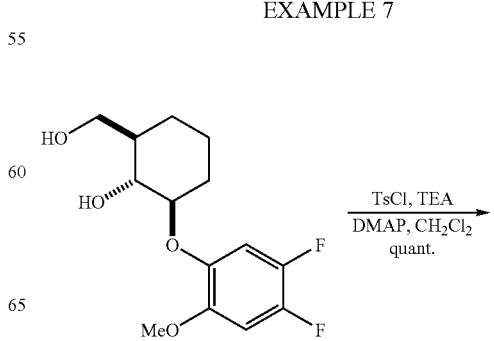

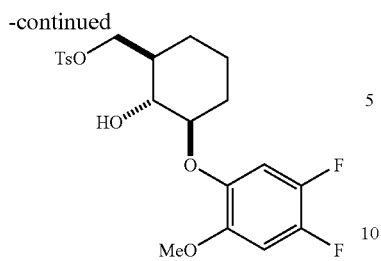

Diol (38 mg, 0.132 mmol) was dissolved in methylene chloride (1.3 mL), followed by adding triethyl amine (37 mL), N,N-dimethylamino pyridine and tosylchloride to react the mixture at room temperature for 6 hr. Thereto, 1N hydrochloric acid was added, followed by extracting a product with ethyl acetate, further followed by washing an organic layer with a saturated sodium hydrogen carbonate aqueous solution and a saturated saline solution. The organic layer was dried over sodium sulfate, filtered and concentrated, to obtain a target object, tosylate (58 mg, yield: quant).

NMR (CDCL$_3$) δ 0.87-0.92 (1H, m), 1.21-1.26 (1H, m), 1.41-1.48 (1H, m), 1.70-1.80 (3H, m), 2.07-2.13 (1H, m), 2.45 (3H, s), 3.40 (1H, s), 3.50 (1H, t, J=9.5 Hz), 3.61-3.66 (1H, m), 4.16 (1H, dd, J=9.5, 6.1 Hz), 4.22 (1H, dd, J=9.5, 3.1 Hz), 6.73 (1H, dd, J=11.0, 7.3 Hz), 6.84 (1H, dd, J=11.0, 7.9 Hz), 7.34 (2H, d, J=7.9 Hz), 7.81 (2H, d, J=8.3 Hz).

EXAMPLE 8

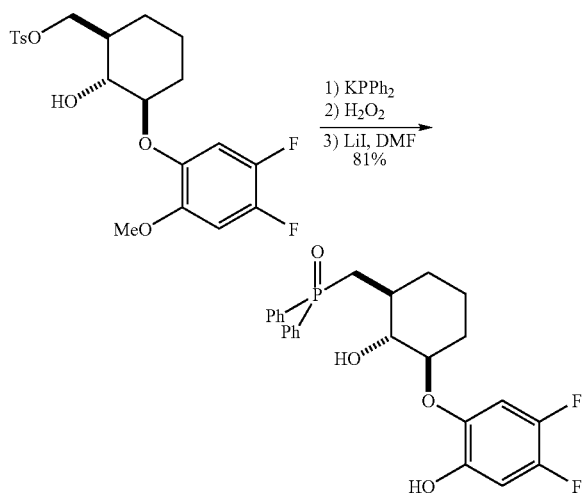

Tosylate (86.3 mg, 0.195 mmol) was dissolved in THF (1 mL), followed by adding potassium diphenyl phosphide (0.5 M in THF, 858 mL, 0.429 mmol) under ice cooling to reacting the mixture for 15 min. Thereafter, hydrogen peroxide water (5 mL) was added, followed by stirring for 30 min, further followed by adding a saturated sodium thiosulfate aqueous solution. After a product was extracted with ethyl acetate, an organic layer was washed with saturated saline solution. The organic layer was dried over sodium sulfate, filtered and concentrated, to obtain a crude product.

The resulting crude product was dissolved in DMF (1 mL), thereto lithium iodide (157 mg, 1.17 mmol) was added, followed by reacting the mixture at 160° C. for 19 hr. After adding water thereto, a product was extracted with ethyl acetate. An organic layer was washed with saturated saline solution, followed by drying over sodium sulfate, further followed by filtering and concentrating, to obtain a target object, phosphine oxide (74.1 mg, yield: 81%).

NMR (CDCL$_3$) δ 1.10-1.19 (1H, m), 1.26-1.35 (2H, m), 1.48-1.57 (1H, m), 1.67-1.80 (2H, m), 2.13-2.18 (1H, m), 2.39-2.44 (2H, m), 3.31-3.37 (1H, m), 3.56 (1H, t, J=9.2 Hz), 6.72 (1H, dd, J=11.6, 8.0 Hz), 6.78 (1H, dd, J=10.7, 8.3 Hz), 7.46-7.60 (6H, m), 7.69-7.78 (5H, m).

EXAMPLE 9

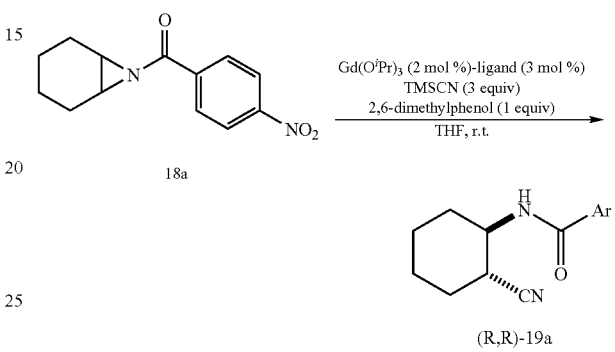

<Aziridine Ring Opening Reaction>

An asymmetric ligand obtained in Example 3 (in Table 1 below, represented by "4" of "ligand", simply represented as "ligand" in the formula) (13.3 mg, 0.03 mmol) was dissolved in 0.6 mL of THF, Gd(O$^i$Pr)$_3$ (0.2 M in THF, 100 μL, 0.02 mmol) was added thereto, followed by stirring at 54° C. for 1 hr. The solvent was distilled away, followed by drying a residue under reduced pressure by use of a vacuum pump for 2 hr. Thereto, aziridine 18a that is a raw material (246 mg, 1.0 mmol), 2,6-dimethylphenol (122 mg, 1.0 mmol) and THF (5 mL) were added, followed by further adding 40 μL of TMSCN (0.30 mmol) at room temperature. After a reaction was carried out for 13 hr, water and ethyl acetate were added to stop a reaction. A product was extracted with ethyl acetate, a collected organic layer was dried over sodium sulfate, followed by filtering and distilling away the solvent, a resulting crude product was purified by use of a silica gel column (hexane:ethyl acetate=3:1 to 3:2), thereby to obtain an aziridine ring opened body 19a at the yield of 99% (269 mg, 0.99 mmol). From the optically active HPLC analysis [Chiralpak AD-H, 2-propanol/hexane 1/9, flow 1.0 mL/min, detection at 254 nm: tR 18.4 min (major) and 2.09 min (minor)], the optical purity was determined to be 98% ee. Example 9 is shown in Table 1 below as "entry" No. "1".

19a: IR (KBr): 3334, 3113, 2950, 2865, 2244, 1647, 1521, 1344, 877, 725 cm$^{-1}$; $^1$H NMR (d-DMSO): δ=8.92 (d, J=8.5 Hz, 1H), 8.35 (d, J=9.0 Hz, 2H), 8.06 (d, J=9.0 Hz, 2H), 4.12-3.97 (m, 1H), 2.86-2.75 (m, 1H), 2.17-2.06 (m, 1H), 1.91-1.81 (m, 1H), 1.77-1.55 (m, 3H), 1.44-1.27 (m, 2H), 1.25-1.12 (m, 1H); $^{13}$C NMR (d-DMSO): δ=164.0, 149.1, 139.8, 128.7, 123.7, 121.3, 49.7, 33.8, 31.7, 28.8, 23.9, 23.8; MS (ESI): m/z 296 [M+Na+]; Anal. calcd for C$_{14}$H$_{15}$N$_3$O$_3$: C, 61.53; H, 5.53; N, 15.38%. Found: C, 61.13; H, 5.61; N, 15.21%; [α]$^{22}_D$ −72.5 (c=0.350, Acetone) (>99% ee).

EXAMPLES 10 to 19

Except that, in place of a ligand in the example 9, a ligand represented by "5" in Table 1 below was used and/or in place of a raw material aziridine 18a in the example 9, each of 18b to 18i was used, an aziridine ring opening reaction was carried out in a manner similar to example 9. Results thereof are shown in Table 1 below. Examples 10 to 19, respectively, are shown by "entry" Nos. "2", "4", "6", "8", "10", "11", "13", "15", "17" and "19".

COMPARATIVE EXAMPLES 1 TO 9

By use of a conventional ligand derived from glucose (ligand represented by "1" in the table 1 below) in place of the ligand in the example 9, a raw material aziridine 18a was subjected to a ring opening reaction in a manner similar to example 9. The result thereof is shown in "entry" No. "3" of Table 1.

Further, except that, in the comparative example 1, in place of a raw material aziridine 18a, by use of each of 18b to 18i, an aziridine ring opening reaction was carried out in a manner similar to example 1. Results thereof are shown in Table 1 below. Comparative examples 2 to 9, respectively, are represented by "entry" Nos. "5", "7", "9", "12", "14", "16", "18" and "20".

When examples and comparative examples that have the same raw materials are compared, it is found that the optical purities of examples (values represented by [ee(%)] in Table 1) are higher than that of the comparative examples. From the foregoing results, it was found that when the ligand according to the present invention is used, in comparison with a conventional ligand derived from glucose, a product is obtained with higher optical purity.

TABLE 1

$$R^1 \text{-aziridine-}C(O)\text{-C}_6H_4\text{-}NO_2 \xrightarrow[\text{THF, temp.}]{\substack{\text{Gd (O}^i\text{Pr})_3 \\ (x \text{ mol \%})\text{-ligand} \\ (1.5x \text{ mol \%}) \\ \text{TMSCN (3 equiv)} \\ 2,6\text{-dimethylphenol} \\ (1 \text{ equiv})}} (R,R)\text{-19}$$

| entry | substrate | ligand | loading (x mol %) | temp. (° C.) | time (h) | yield$^a$ (%) | ee$^b$ (%) |
|---|---|---|---|---|---|---|---|
| 1 | (cyclohexene-fused aziridine) | 18a | 4 | 2 | r.t | 13 | 98 | 98$^f$ |
| 2$^c$ | | | 5 | 1 | 40 | 3 | 99 | 99$^f$ |
| 3$^d$ | | | 1 | 10 | 0 | 20 | 94 | 87$^g$ |
| 4 | (cyclohexadiene-fused aziridine) | 18b | 4 | 2 | 40 | 12 | 83 | 96 |
| 5$^d$ | | | 1 | 10 | r.t. | 95 | 85 | 82 |
| 6 | (benzofused aziridine) | 18c | 4 | 2 | 40 | 14 | 98 | 95 |
| 7$^d$ | | | 1 | 10 | r.t. | 42 | 91 | 83 |
| 8 | (cyclopentane-fused aziridine) | 18d | 4 | 2 | 40 | 14 | 98 | 98$^f$ |
| 9$^d$ | | | 1 | 10 | 40 | 14 | 98 | 91$^g$ |
| 10 | (CbzN-pyrrolidine-fused aziridine) | 18e | 4 | 2 | 40 | 22 | 99 | 96 |
| 11$^c$ | | | 5 | 2 | 40 | 74 | 99 | 96 |
| 12$^d$ | | | 1 | 20 | 60 | 23 | 89 | 84 |
| 13 | (O-tetrahydrofuran-fused aziridine) | 18f | 4 | 2 | 60 | 28 | 84 | 96 |
| 14$^d$ | | | 1 | 20 | 60 | 96 | 92 | 84 |
| 15 | (cycloheptane-fused aziridine) | 18g | 4 | 5 | 67 | 15 | 99 | 95 |
| 16$^d$ | | | 1 | 10 | 60 | 64 | 92 | 80 |
| 17 | (gem-dimethyl aziridine) | 18h | 4 | 2 | 40 | 14 | 98 | 98$^f$ |
| 18$^d$ | | | 1 | 10 | r.t. | 39 | 93 | 85$^g$ |

TABLE 1-continued

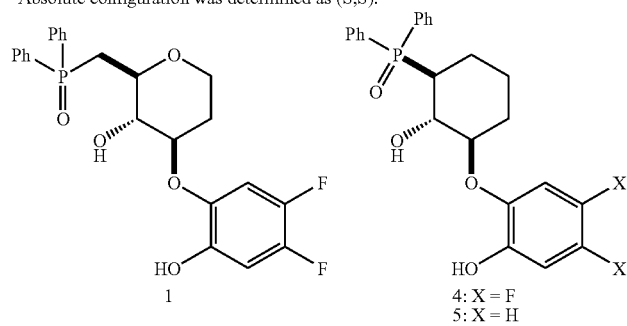

| entry | substrate | ligand | loading (x mol %) | temp. (° C.) | time (h) | yield[a] (%) | ee[b] (%) |
|---|---|---|---|---|---|---|---|
| 19 | Ph, Ph, NR² | 18l | 4 | 5 | 67 | 4 | 95 (47/53)[e] | 93/93 |
| 20[d] | | | 1 | 10 | r.t. | 96 | 81 (54/46)[e] | 90/80 |

[a] Isolated yield.
[b] Determined by chiral HPLC.
[c] in the presence of 10 mol % of 2,6-dimethylphenol at room temperature.
[d] Using a catalyst generated from 10 mol % of Gd (O^iPr)₃ and 20 mol % of 1 in the presence of 5 mol % of TFA and 1 equiv of 2,8-dimethylphenol in propionitrile at 0° C.
[e] Ratio of diastereomers determined by 1H NMR.
[f] Absolute configuration was determined as (R,R).
[g] Absolute configuration was determined as (S,S).

EXAMPLE 20

<Cyano-Michael Addition Reaction>

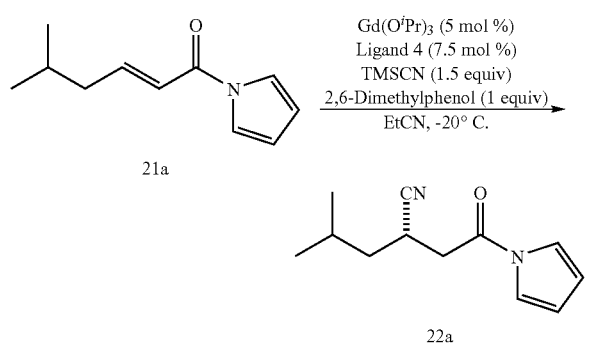

An asymmetric ligand obtained in example 3 (in Table 1, represented by "4" of "ligand") (6.7 mg, 0.015 mmol) was dissolved in 0.3 mL of THF, Gd(O^iPr)₃ (0.2 M in THF, 50 μL, 0.01 mmol) was added at room temperature, followed by stirring at 54° C. for 1 hr. A solvent was distilled away and a residue was dried under reduced pressure by use of a vacuum pump for 2 hr. Thereto, 2,6-dimethyl phenol (24.4 mg, 0.2 mmol) was added, followed by adding a raw material 21a (35.4 mg, 0.2 mmol) after dissolving in 0.2 mL of THF. A reaction solution was cooled to −20° C. and TMSCN (40 mL, 0.30 mmol) was added thereto. After 5.5 hr, silica gel was added to stop the reaction, followed by loading to a silica gel column and eluting at hexane:ethyl acetate=10:1 to 4:1 to purify, thereby 22a was obtained by 40.5 mg at the yield of 99%. From the optically active HPLC analysis [Chiralcel OD-H, 2-propanol/hexane 1/20, flow 1.0 mL/min, detection at 254 nm: tR 13.0 min (minor) and 16.7 min (major)], the optical purity was determined to be 93% ee. Example 20 is shown in Table 2 below as "entry" No. "1".

22a: IR (KBr): 3402, 3145, 2960, 2931, 2242, 1708, 1474, 1374, 1292, 921 cm⁻¹; ¹H NMR (CDCl₃): δ=7.27 (brs, 2H), 6.32 (t, J=2.3 Hz, 2H), 3.33-3.16 (m, 2H), 3.06 (dd, J=6.1, 16.7, 1H), 1.98-1.82 (m, 1H), 1.75-1.57 (m, 1H), 1.49-1.34 (m, 1H), 1.00 (d, J=6.4 Hz, 3H), 0.99 (d, J=6.7 Hz, 3H); ¹³C NMR (CDCl₃): d=166.5, 121.1, 118.8, 113.9, 40.8, 37.3, 26.2, 25.0, 22.9, 21.1; MS: m/z 204 [M⁺]; Anal. calcd for C₁₂H₁₆N₂O: C, 70.56; H, 7.90; N, 13.71%. Found: C, 70.48; H, 8.03; N, 13.74%; [α]²⁵_D −26.2 (c=0.940, CHCl₃) (97% ee).

EXAMPLES 21 to 27

Except that, in the example 20, an amount of Gd(O$^i$Pr)$_3$ and an amount of the ligand were varied and/or, in place of the raw material 21a in the example 20, each of 21b to 21h were used, a cyano-Michael addition reaction was carried out in a manner similar to example 9. The results thereof are shown in Table 2 below. In Table 2, examples 21 to 27, respectively, are shown with "entry" Nos. "2", "4", "6", "8", "10", "12" and "14".

COMPARATIVE EXAMPLES 10 TO 16

By use of a conventional ligand derived from glucose (ligand represented by "1" in the table 1 and Table 2 below) in place of the ligand in the example 20, a cyano-Michael addition reaction was carried out with a raw material 21a in a manner similar to example 20. The result thereof is shown in "entry" No. "3" of Table 2.

Further, except that, in the comparative example 10, in place of a raw material 21a, each of 21b to 21h was used, a cyano-Michael addition reaction was carried out in a manner similar to comparative example 10. Results thereof are shown in Table 2 below. Comparative examples 11 to 16, respectively, are shown by "entry" Nos. "5", "7", "9", "11", "13" and "15".

When examples and comparative examples that have the same raw materials are compared, it is found that the optical purities of examples (values represented by "ee(%)" in Table 2) are equal to or higher than that of the comparative examples. From the foregoing results, it was found that when the ligand according to the present invention is used, in comparison with a conventional ligand derived from glucose, a product is obtained with equal or higher optical purity.

TABLE 2

Reaction scheme: Substrate 21 (R-CH=CH-C(O)-N-pyrrolyl) reacts with Gd(O$^i$Pr)$_3$ (x mol %), Ligand 4 (1.6x mol %), TMSCN (1.5 equiv), 2,6-Dimethylphenol (1 equiv) in EtCN at −20 °C to give product 22 (R-CH(CN)-CH$_2$-C(O)-N-pyrrolyl).

| entry | substrate | ligand | x (mol %) | time (h) | yield (%)$^a$ | ee (%)$^b$ |
|---|---|---|---|---|---|---|
| 1 | (CH$_3$)$_2$CHCH$_2$CH=CH-C(O)-pyrrolyl | 21a | 4 | 5 | 5.5 | 99 | 93$^d$ |
| 2 | | | 4 | 2 | 14 | 99 | 93$^d$ |
| 3$^c$ | | | 1 | 5 | 42 | 89 | 97$^e$ |
| 4 | CH$_3$CH$_2$CH$_2$CH=CH-C(O)-pyrrolyl | 21b | 4 | 5 | 2.5 | 93 | 93$^d$ |
| 5$^c$ | | | 1 | 5 | 42 | 91 | 98$^e$ |
| 6 | (CH$_3$)$_3$C-CH=CH-C(O)-pyrrolyl | 21c | 4 | 5 | 2.5 | 95 | 96 |
| 7$^c$ | | | 1 | 5 | 88 | 87 | 90 |
| 8 | Ph-CH$_2$CH$_2$CH$_2$CH=CH-C(O)-pyrrolyl | 21d | 4 | 5 | 24 | 96 | 86 |
| 9$^c$ | | | 1 | 5 | 43 | 92 | 96 |
| 10 | Ph-CH=CH-C(O)-pyrrolyl | 21e | 4 | 5 | 38 | 91 | 88$^d$ |
| 11$^c$ | | | 1 | 10 | 98 | 90 | 91$^e$ |

TABLE 2-continued

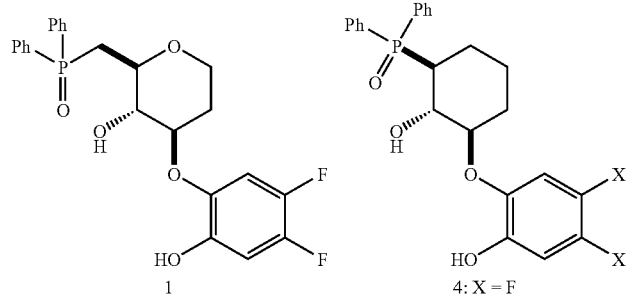

| entry | substrate | ligand | x (mol %) | time (h) | yield (%)[a] | ee (%)[b] |
|---|---|---|---|---|---|---|
| 12 | | 21f | 4 | 10 | 20 | 89 | 95 |
| 13[c] | | | 1 | 10 | 88 | 91 | 89 |
| 14 | | 21h | 4 | 5 | 1 | 92 (5.7.1) | 76/12 |
| 15[c] | | | 1 | 5 | 8 | 99 (1.1/1) | 88/83 |

[a] isolated yield.
[b] Determined by chiral HPLC.
[c] Using a catalyst generated from Gd (O*i*Pr)$_3$ and 1 in a 1:2 ratio with 0.5 equiv of TMSCN and 2 equiv of HCN.
[d] Absolute configuration was determined as shown in the scheme.
[e] Absolute configuration was opposite to the one shown in the scheme.

EXAMPLE 28

<Conversion from 22a to Antiepileptic Agent Pregabalin>

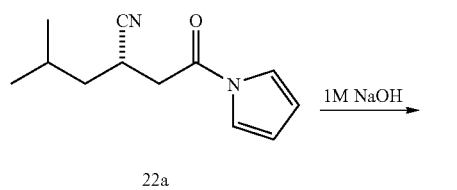

22a

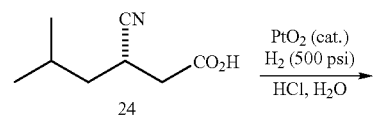

24

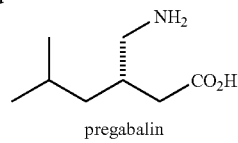

pregabalin

To a THF solution (0.44 mL) of a compound 22a (44.8 mg, 0.219 mmol) obtained in example 20, a 1 M NaOH aqueous solution (0.44 mL) was added at room temperature. After 1 hr, THF was distilled away under reduced pressure, thereto a saturated sodium hydrogen carbonate aqueous solution was added, followed by washing an aqueous layer with methylene chloride three times. The aqueous layer was controlled to pH=1 by adding hydrochloric acid and methylene chloride was used to extract. Organic layers were combined, followed by drying over sodium sulfate, further followed by filtering and distilling away the solvent, thereby to obtain 31.8 mg (94%) of 24.

24: IR (neat): 2961, 2244, 1714, 1469, 1414, 1371, 1175, 924, 619 cm$^{-1}$; $^1$H NMR (CDCl$_3$): δ=9.29 (brs, 1H), 3.12-2.96 (m, 1H), 2.76 (dd, J=7.5, 17.0 Hz, 1H), 2.62 (dd, J=6.1, 17.0 Hz, 1H), 1.95-1.78 (m, 1H), 1.74-1.57 (m, 1H), 1.43-1.30 (m, 1H), 0.98 (d, J=6.7 Hz, 3H), 0.96 (d, j=6.7 Hz, 3H); $^{13}$C NMR (CDCl$_3$): □=175.5, 120.8, 40.6, 36.8, 26.1, 25.5, 22.8, 21.2; MS: m/z 155 [M$^+$]; HRMS (EI): m/z calcd for C$_8$H$_{14}$NO$_2$ [M+H$^+$]: 156.1025. Found: 156.1026; $[α]^{21}_D$ −15.0 (c=0.590, CHCl$_3$). Observed value: $[α]^{25}_D$ −16.7 (c=0.5, CHCl$_3$) (J. Am. Chem. Soc. 2003, 125, 4442).

The compound 24 obtained in the example is readily converted to Pregabalin by reference to a prior literature (J. Am. Chem. Soc. 2003, 125, 4442).

Thus, when by use of examples 20 and 28, intermediate bodies are obtained at a smaller quantity of catalyst at a shorter time; accordingly, a precursor 24 of an antiepileptic agent Pregabalin is obtained efficiently more than ever.

EXAMPLE 29

Except that, in example 2, monomethylchlorocatechol was used in place of monomethyldifluorocatechol, an asymmetric ligand where X=Cl in "ligand 2" of the following formula was prepared in a manner similar to examples 1 to 3.

$^1$H NMR (CDCl$_3$): δ=9.28 (s, 1H), 7.74-7.70 (m, 4H), 7.62-7.47 (m, 6H), 7.03 (s, 1H), 6.98 (s, 1H), 6.84 (bs, 1H), 4.00 (dd, J=18.6, 8.5 Hz, 1H), 3.64-3.59 (m, 1H), 2.64 (ddd, J=22.9, 12.1, 3.3 Hz, 1H), 2.19-2.16 (m, 1H), 1.81-1.69 (m, 2H), 1.48-1.28 (m, 2H), 1.09-1.00 (m, 1H).

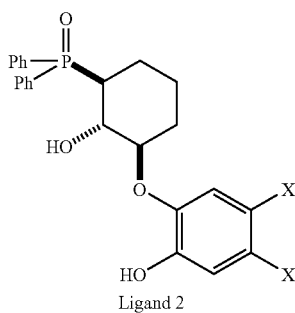

Ligand 2

EXAMPLE 30

In a well-dried and argon-substituted test tube, an asymmetric ligand (0.02 mmol) prepared in example 3 was added, followed by adding THF (0.323 mmol). Thereto, 100 mL of a THF solution of Ba(OPr)$_2$, left standing for 1 hr after the solution was diluted to be 0.2 M, was gradually added at room temperature. After stirring at 50° C. for 1 hr, the solvent was distilled away, followed by drying under vacuum at room temperature for 3 hr. A residual was dissolved in CH$_2$Cl$_2$ (300 mL) and cooled to −20° C. Thereto, diene (52.9 ml, 0.3 mmol) and dienophile (0.5 M CH$_2$Cl$_2$ solution 200 mL, 0.1 mmol) were added, followed by stirring until the raw material disappears. After heating to room temperature, acetic acid (ca. 75 mL) and TBAF (0.1 M THF solution, 800 mL, 0.8 mmol) were added, followed by stirring for 5 min. A saturated sodium hydrogen carbonate aqueous solution was carefully added and an aqueous phase was extracted with ethyl acetate, followed by washing an organic phase with saturated saline solution. Sodium sulfate was used to dry, followed by filtering and distilling away a solvent, further followed by silica gel column chromatography, a target subject was obtained as a mixture of diastereomer.

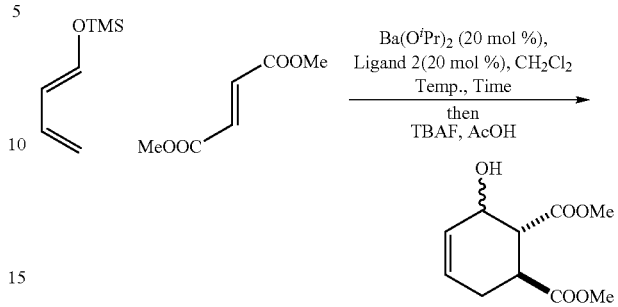

For α alcohol: $^1$H NMR (CDCl$_3$, 500 MHz) δ 5.88 (m, 2H), 4.49 (m, 1H), 3.72 (s, 3H), 3.69 (s, 3H), 2.99 (ddd, J=5.5, 11.3, 11.8 Hz, 1H), 2.92 (dd, J=4.0, 11.8 Hz, 1H), 2.48-2.43 (m, 1H), 2.16-2.10 (m, 1H); For β alcohol: $^1$H NMR (CDCl$_3$, 500 MHz) d 5.77-5.73 (m, 1H), 5.70-5.67 (m, 1H), 4.42 (m, 1H), 3.73 (s, 3H), 3.67 (s, 3H), 2.96-2.92 (m, 1H), 2.76 (dd, J=8.9, 11.3 Hz, 1H), 2.41-2.36 (m, 1H), 2.26-2.20 (m, 1H); For diastereomer mixture: $^{13}$C NMR (CDCl$_3$, 125 MHz) δ 175.5, 174.1, 174.0, 172.8, 129.4, 128.9, 127.1, 126.3, 68.5, 63.9, 52.2, 52.1, 52.0, 52.0, 49.8, 47.6, 40.7, 36.2, 28.7, 27.7; IR (neat, cm$^{-1}$) 3460, 2953, 1736; ESI-MS m/z 237 [M+Na]$^+$; GC (CHIRASIL-DEX CB, column temperature 150° C., injection temperature 200° C., detection temperature 250° C.): t$_R$ 12.2 min (endo/exo mixture), 13.3 min (endo, major), 13.8 min (endo, minor).

EXAMPLES 31 to 33

Except that, in the example 30, X of Ligand 2 was changed to Cl (asymmetric ligand of example 29) or F and/or a reaction time and/or a reaction temperature in the example 30 were changed, similarly to example 30, reactions were carried out. Results thereof are shown in Table 3 below.

COMPARATIVE EXAMPLE 17

Except that, in place of a ligand in the example 30, a conventional glucose-derived ligand (ligand represented by "1" in the tables 1 and 2) was used, a reaction was carried out in a manner similar to example 30. Results thereof are shown in Table 3 below.

When example 33 and comparative example 17 are compared, it is found that the optical purity of a product of example 33 is higher. Further, when examples 30 to 33 are compared, it is found that a ligand having a substituent group of chlorine or fluorine in a catechol site are higher in the endo/exo ratio and yield.

TABLE 3

| | X | Temperature | Hours | Yield | Endo/exo | Optical Purity |
|---|---|---|---|---|---|---|
| Example 30 | F | Room Temp. | 11 h | <6% | 0.8:1 | 88% ee |
| Example 31 | H | −20° C. | 1.5 h | 34% | 4.6:1 | 88% ee |
| Example 32 | Cl | −20° C. | 47 h | 44% | 11.5:1 | 90% ee |
| Example 33 | F | −20° C. | 47 h | 48% | 13.3:1 | 86% ee |
| Comparative Example 17 | — | −20° C. | 42 h | 74% | 3.3:1 | 61% ee |

Figure 1:
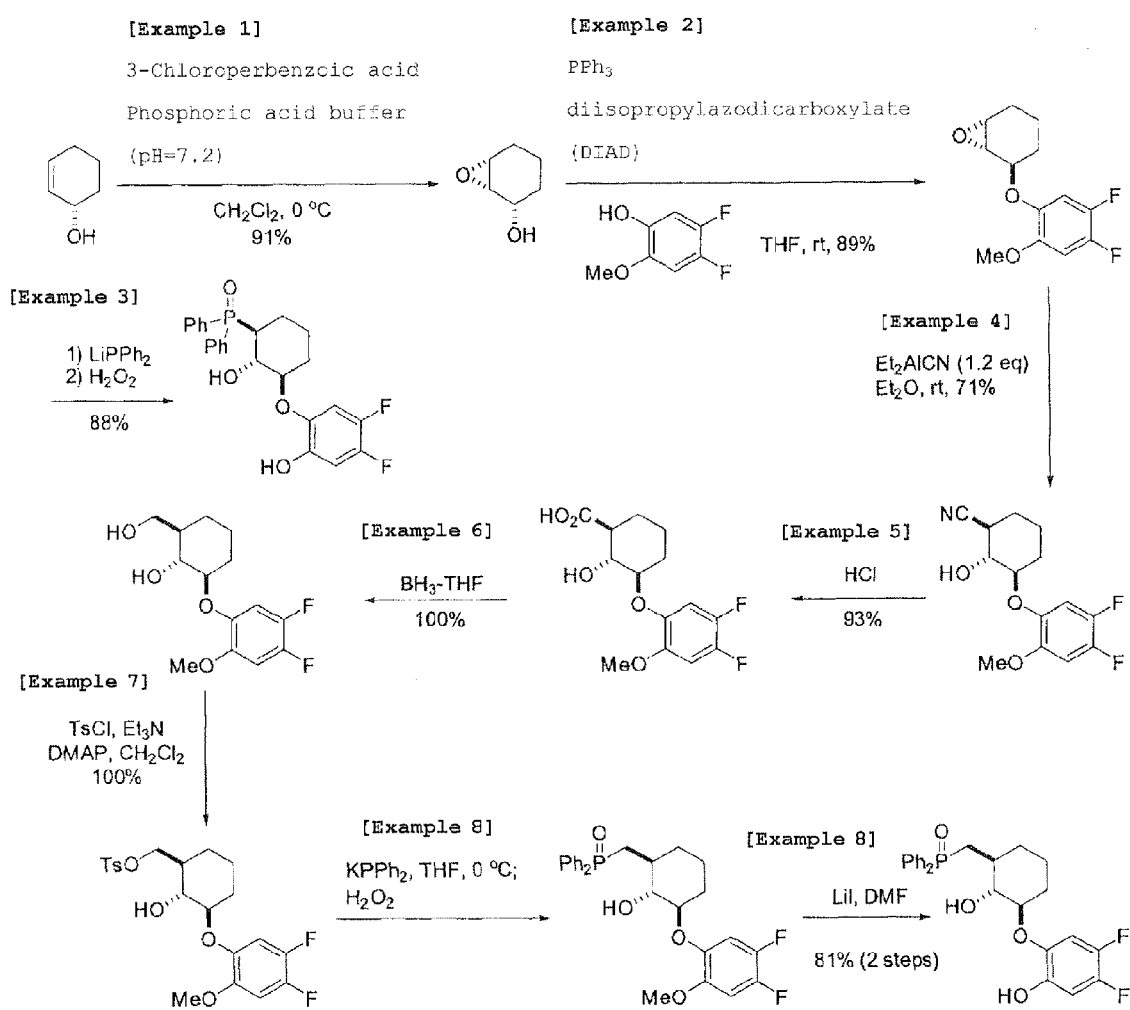
FIG. 1 is a scheme surveying examples 1 to 8.

What is claimed is:

1. A ligand represented by following general formula I:

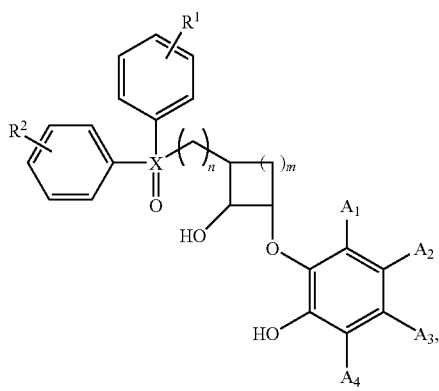

wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —$OR^a$ ($R^a$ represents a linear or branched alkyl group having 1 to 4 carbon atoms), an amino group represented by —$NR^bR^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$.

2. A ligand represented by following general formula Ia:

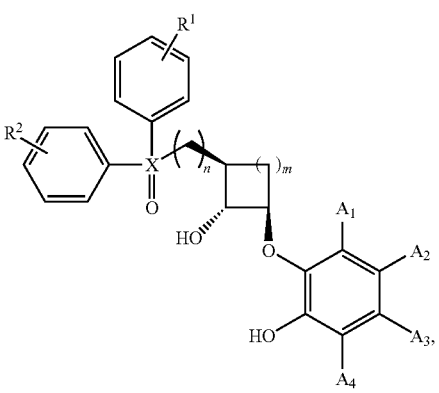

wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —$OR^a$ ($R^a$ represents a linear or branched alkyl group having 1 to 4 carbon atoms), an amino group represented by —$NR^bR^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$.

3. A ligand represented by following general formula Ib:

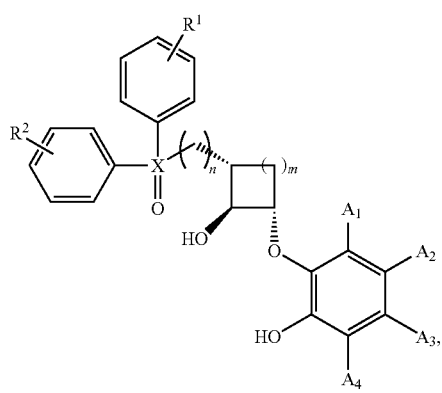

wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —$OR^a$ ($R^a$ represents a linear or branched alkyl group having 1 to 4 carbon atoms), an amino group represented by —$NR^bR^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$.

4. The ligand according to claim 1, wherein n is an integer of 0 or 1.

5. The ligand according to claim 1, wherein m is an integer of 2 to 4.

6. The ligand according to claim 1, wherein two of the $A_1$ to $A_4$ are hydrogen atoms and the other two thereof are fluorine atoms.

7. A method of producing a ligand represented by following general formula I from a compound represented by following general formula II:

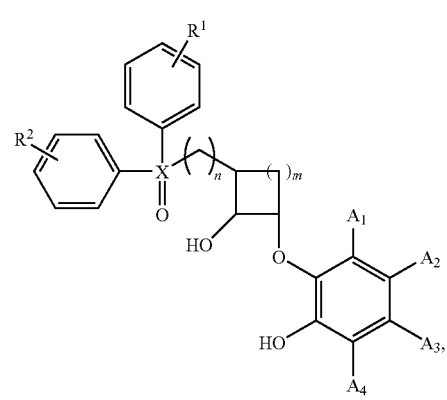

wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —$OR^a$ ($R^a$ represents a linear or branched alkyl group having 1 to 4 carbon atoms), an amino group represented by —$NR^bR^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$, and

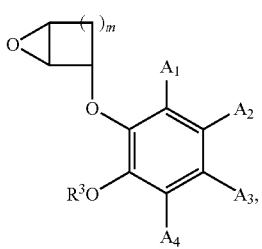

II wherein $R^3$ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of $A_1$ to $A_4$ independently has the same definition as described above, the method comprising the steps of:
a) reacting the compound represented by the general formula II with a metal salt of diphenylphosphine, diarylphosphine or diarylamine;
b) thereafter, processing with ammonium chloride and hydrogen peroxide; and
b') when X is As or N and $R^3$ is one other than a hydrogen atom, allowing palladium-carbon to react with hydrogen, lithium chloride, dichlorodicyanobenzoquinone, cerium ammonium nitrate or a fluorine anion to make the $R^3$ a hydrogen atom, to obtain the ligand represented by the general formula I.

8. The method according to claim 7, wherein the compound represented by the general formula II is obtained by c) reacting a compound represented by following general formula III, wherein m has the same definition as described above, in the presence of diethylazodicarboxylate or diisopropylazodicarboxylate and triphenylphosphine or tributylphosphine, with a compound represented by following general formula IV, wherein $R^3$ and $A_1$ to $A_4$ have the same definitions as described above:

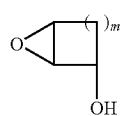

III

-continued

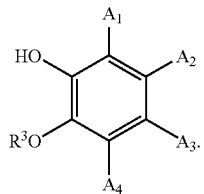

IV

9. The method according to claim 8, wherein the compound represented by the general formula III is obtained by d) reacting a compound represented by following general formula V, wherein m has the same definition as described above, in the presence of a phosphoric acid buffer, with a peracid:

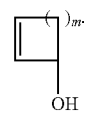

V

10. A method of producing a ligand represented by following general formula Ia from a compound represented by following general formula IIa:

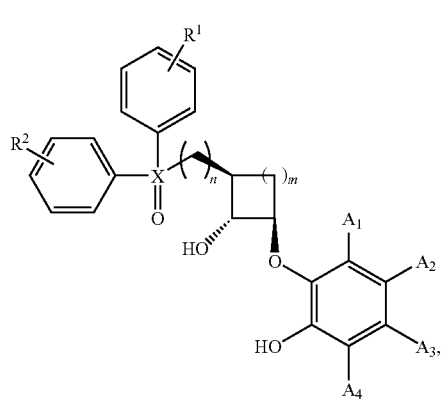

Ia wherein each of $R^1$ and $R^2$ independently represents 0 to 5 substituent groups; X represents P, As or N; in represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —$OR^a$ ($R^a$ represents a linear or branched alkyl group having 1 to 4 carbon atoms), an amino group represented by —$NR^bR^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$, and

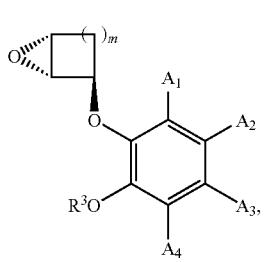

IIa wherein R³ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of $A_1$ to $A_4$ independently has the same definition as described above, the method comprising the steps of:
  a) reacting the compound represented by the general formula IIa with a metal salt of diphenylphosphine, diarylphosphine or diarylamine;
  b) thereafter, processing with ammonium chloride and hydrogen peroxide; and
  b') when X is As or N and R³ is one other than a hydrogen atom, allowing palladium-carbon to react with hydrogen, lithium chloride, dichlorodicyanobenzoquinone, cerium ammonium nitrate or a fluorine anion to make the R³ a hydrogen atom, to obtain the ligand represented by the general formula Ia.

11. The method according to claim 10, wherein the compound represented by the general formula IIa is obtained by c) reacting a compound represented by following general formula IIIa, wherein in has the same definition as described above, in the presence of diethylazodicarboxylate or diisopropylazodicarboxylate and triphenylphosphine or tributylphosphine, with a compound represented by following general formula IV, wherein R³ and $A_1$ to $A_4$ have the same definitions as described above:

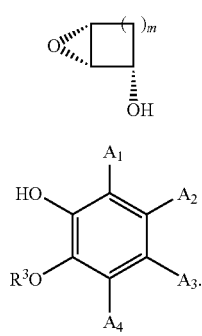

IIIa

IV

12. The method according to claim 11, wherein the compound represented by the general formula IIIa is obtained by d) reacting a compound represented by following general formula Va, wherein m has the same definition as described above, in the presence of a phosphoric acid buffer, with a peracid:

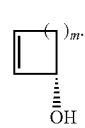

Va

13. A method of producing a ligand represented by following general formula Ib from a compound represented by following general formula IIb:

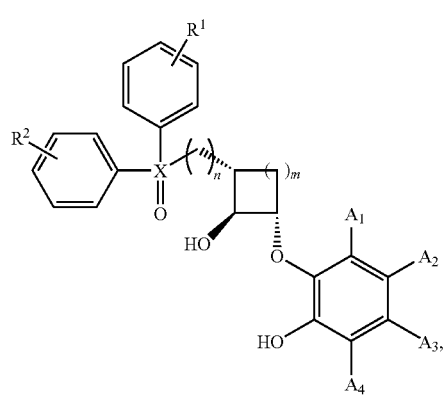

Ib wherein each of R¹ and R² independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —OR$^a$ (R$^a$ represents a linear or branched alkyl group having 1 to 4 carbon atoms), an amino group represented by —NR$^b$R$^c$ (each of R$^b$ and R$^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$, and

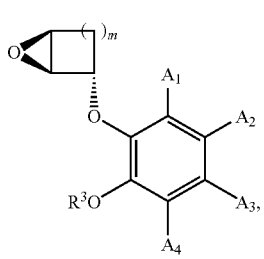

IIb wherein R³ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of $A_1$ to $A_4$ independently has the same definition as described above, the method comprising the steps of:
  a) reacting the compound represented by the general formula IIb with a metal salt of diphenylphosphine, diarylphosphine or diarylamine;

b) thereafter, processing with ammonium chloride and hydrogen peroxide; and b') when X is As or N and $R^3$ is one other than a hydrogen atom, allowing palladium-carbon to react with hydrogen, lithium chloride, dichlorodicyanobenzoquinone, cerium ammonium nitrate or a fluorine anion to make the $R^3$ a hydrogen atom, to obtain the ligand represented by the general formula Ib.

14. The method according to claim 13, wherein the compound represented by the general formula IIb is obtained by c) reacting a compound represented by following general formula IIIb, wherein m has the same definition as described above, in the presence of diethylazodicarboxylate or diisopropylazodicarboxylate and triphenylphosphine or tributylphosphine, with a compound represented by following general formula IV, wherein $R^3$ and $A_1$ to $A_4$ have the same definitions as described above:

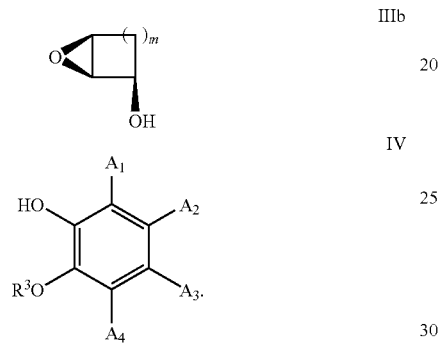

IIIb

IV

15. The method according to claim 14, wherein the compound represented by the general formula IIIb is obtained by d) reacting a compound represented by following general formula Vb, wherein m has the same definition as described above, in the presence of a phosphoric acid buffer, with a peracid:

Vb

16. A producing method of a ligand represented by following general formula I from a compound represented by following general formula II:

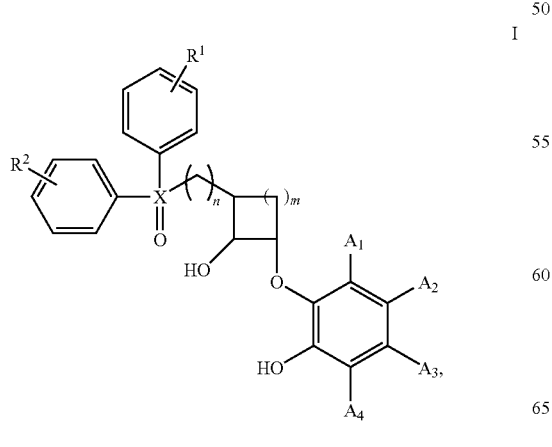

I wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by $—OR^a$ ($R^a$ represents a linear or branched alkyl group having 1 to 4 carbon atoms), an amino group represented by $—NR^bR^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$, and

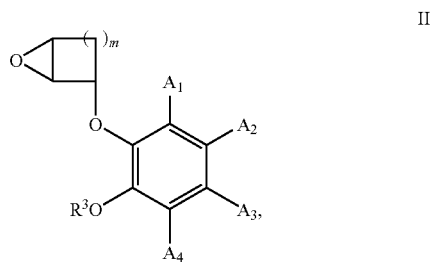

II wherein $R^3$ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of $A_1$ to $A_4$ independently has the same definition as described above, the method comprising the steps of:

g) reacting the compound represented by the general formula II with diethylaluminum cyanide, followed by reacting with concentrated hydrochloric acid, to obtain a compound represented by following general formula VII, wherein m, $R^3$ and $A_1$ to $A_4$ have the same definitions as described above;

h) reacting the compound represented by the general formula VII with a BH$_3$ tetrahydrofuran complex, a BH$_3$ dimethylsulfide complex or LiAlH$_4$, to obtain a compound represented by following general formula VIII, wherein m, $R^3$ and $A_1$ to $A_4$ have the same definitions as described above;

j) reacting the compound represented by the general formula VIII with p-toluenesulfonyl chloride, to obtain a compound represented by following general formula IX, wherein Ts represents a p-toluenesulfonyl group; and m, $R^3$ and $A_1$ to $A_4$ have the same definitions as described above;

k) reacting the compound represented by the general formula IX with potassium diphenyl phosphide, followed by reacting with hydrogen peroxide, to obtain a compound represented by following general formula X, wherein m, $R^3$ and $A_1$ to $A_4$ have the same definitions as described above; and l) reacting the compound represented by the general formula X with lithium iodide, to obtain the ligand represented by the general formula I:

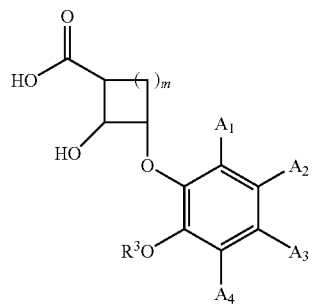

VII

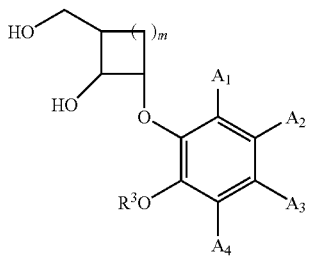

VIII

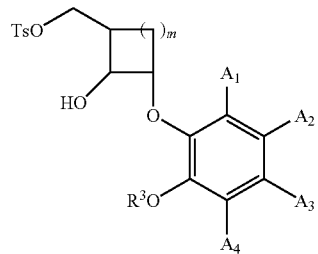

IX

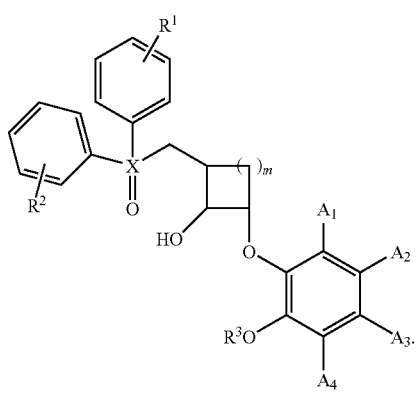

X

17. A method of producing a ligand represented by following general formula Ia from a compound represented by following general formula IIa:

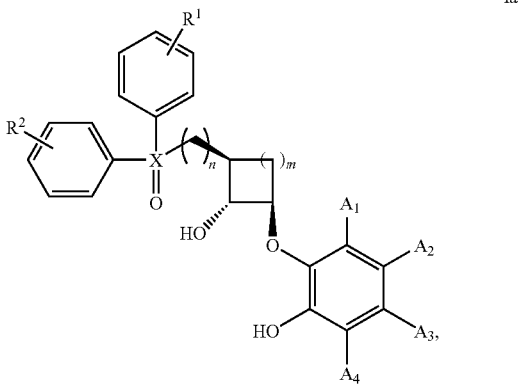

Ia wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —$OR^a$ ($R^a$ represents a linear or branched alkyl group having 1 to 4 carbon atoms), an amino group represented by —$NR^b R^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$, and

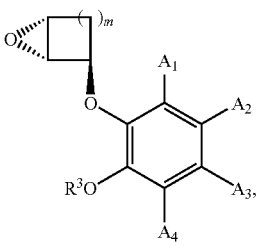

IIa wherein $R^3$ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of $A_1$ to $A_4$ independently has the same definition as described above, the method comprising the steps of:

g) reacting a compound represented by the general formula IIa with diethylaluminum cyanide, followed by reacting with concentrated hydrochloric acid, to obtain a compound represented by following general formula VIIa, wherein m, $R^3$ and $A_1$ to $A_4$ have the same definitions as described above;

h) reacting the compound represented by the general formula VIIa with a $BH_3$ tetrahydrofuran complex, a $BH_3$ dimethyl sulfide complex or $LiAlH_4$, to obtain a compound represented by following general formula VIIIa, wherein m, $R^3$ and $A_1$ to $A_4$ have the same definitions as described above;

j) reacting the compound represented by the general formula VIIIa with p-toluenesulfonyl chloride, to obtain a compound represented by following general formula IXa, wherein Ts represents a p-toluenesulfonyl group, and m, $R^3$ and $A_1$ to $A_4$ have the same definitions as described above;

k) reacting the compound represented by the general formula IXa with potassium diphenyl phosphide, followed by reacting with hydrogen peroxide, to obtain a compound represented by following general formula Xa, wherein m, $R^3$ and $A_1$ to $A_4$ have the same definitions as described above; and l) reacting the compound represented by the general formula Xa with lithium iodide, to obtain the ligand represented by the general formula Ia:

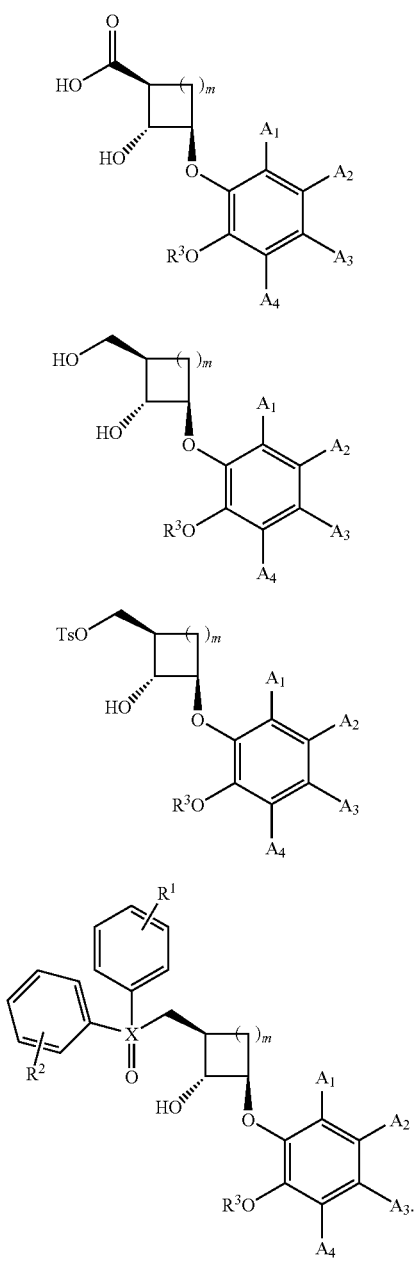

18. A method of producing a ligand represented by following general formula Ib from a compound represented by following general formula IIb:

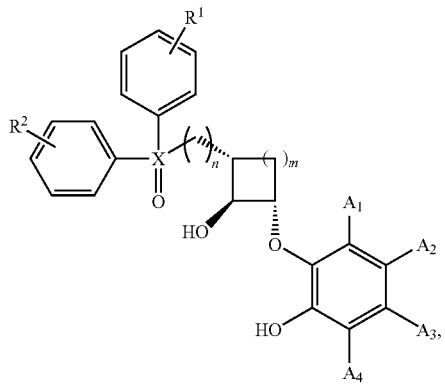

wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —$OR^a$ ($R^a$ represents a linear or branched alkyl group having 1 to 4 carbon atoms), an amino group represented by —$NR^b R^c$ (each of $R^b$ and $R^c$ independently represents a hydrogen atom or a linear or branched alkyl group having 1 to 4 carbon atoms), a linear or branched alkyl group having 1 to 4 carbon atoms, a hydroxyl group or a ring formed of $A_2$ and $A_3$, and

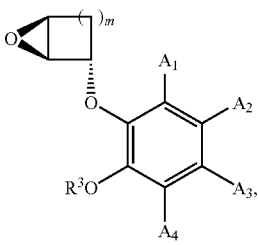

wherein $R^3$ represents a hydrogen atom, a linear or branched alkyl group having 1 to 8 carbon atoms, a linear or branched alkenyl group having 2 to 8 carbon atoms, a benzyl group, a paramethoxy benzyl group or a silyl group; m has the same definition as described above; and each of $A_1$ to $A_4$ independently has the same definition as described above, the method comprising the steps of:

g) reacting a compound represented by the general formula IIb with diethylaluminum cyanide, followed by reacting with concentrated hydrochloric acid, to obtain a compound represented by following general formula VIIb, wherein m, $R^3$ and $A_1$ to $A_4$ have the same definitions as described above;

h) reacting the compound represented by the general formula VIIb with a $BH_3$ tetrahydrofuran complex, a $BH_3$ dimethylsulfide complex or $LiAlH_4$, to obtain a compound represented by following general formula VIIIb, wherein m, $R^3$ and $A_1$ to $A_4$ have the same definitions as described above;

j) reacting the compound represented by the general formula VIIIb with p-toluenesulfonyl chloride, to obtain a compound represented by following general formula IXb, wherein Ts represents a p-toluenesulfonyl group, and m, R³ and A₁ to A₄ have the same definitions as described above;

k) reacting the compound represented by the general formula IXb with potassium diphenyl phosphide, followed by reacting with hydrogen peroxide, to obtain a compound represented by following general formula Xb, wherein m, R³ and A₁ to A₄ have the same definitions as described above; and l) reacting the compound represented by the general formula Xb with lithium iodide, to obtain the ligand represented by the general formula Ib:

19. A catalyst being formed of:

A) a metal alkoxide or a metal amide represented by $M_x(OR^4)_y$ or $M_{x'}(NR^5)_{y'}$, wherein M is a metal selected from the group consisting of titanium, zirconium, aluminum, gallium, barium and rare earth elements; each of $R^4$ and $R^5$ independently represents a substituted or non-substituted, linear or branched or cyclic alkyl group having 2 to 6 carbon atoms, a substituted or non-substituted, linear or branched or cyclic alkenyl group, a substituted or non-substituted aromatic group or a trialkylsilyl group, and x and y and x' and y' are integers stoichiometrically determined by the metal M; and B) a ligand represented by following general formula I, wherein each of $R^1$ and $R^2$ independently represents 0 to 5 substituent groups; X represents P, As or N; m represents an integer of 0 to 7; n represents an integer of 0 to 3; and each of $A_1$ to $A_4$ independently represents a hydrogen atom, a fluorine atom, a chlorine atom, a bromine atom, a benzoyl group, an acetyl group, a nitro group, a trifluoroacetyl group, a trifluoromethyl group, an alkoxy group represented by —OR$^a$ (R$^a$ represents a linear or branched alkyl group having 1 to 4 carbon atoms), an amino group represented by —NR$^b$R$^c$ (each of R$^b$ and R$^c$ independently represents a hydrogen atom, or a linear or branched alkyl group having 1 to 4 carbon atoms), a linear or branched alkyl group having 1 to 4 carbon atoms, a hydroxyl group or a ring formed of $A_2$ and $A_3$:

20. The catalyst according to claim 19, wherein the B) ligand is represented by following general formula Ia:

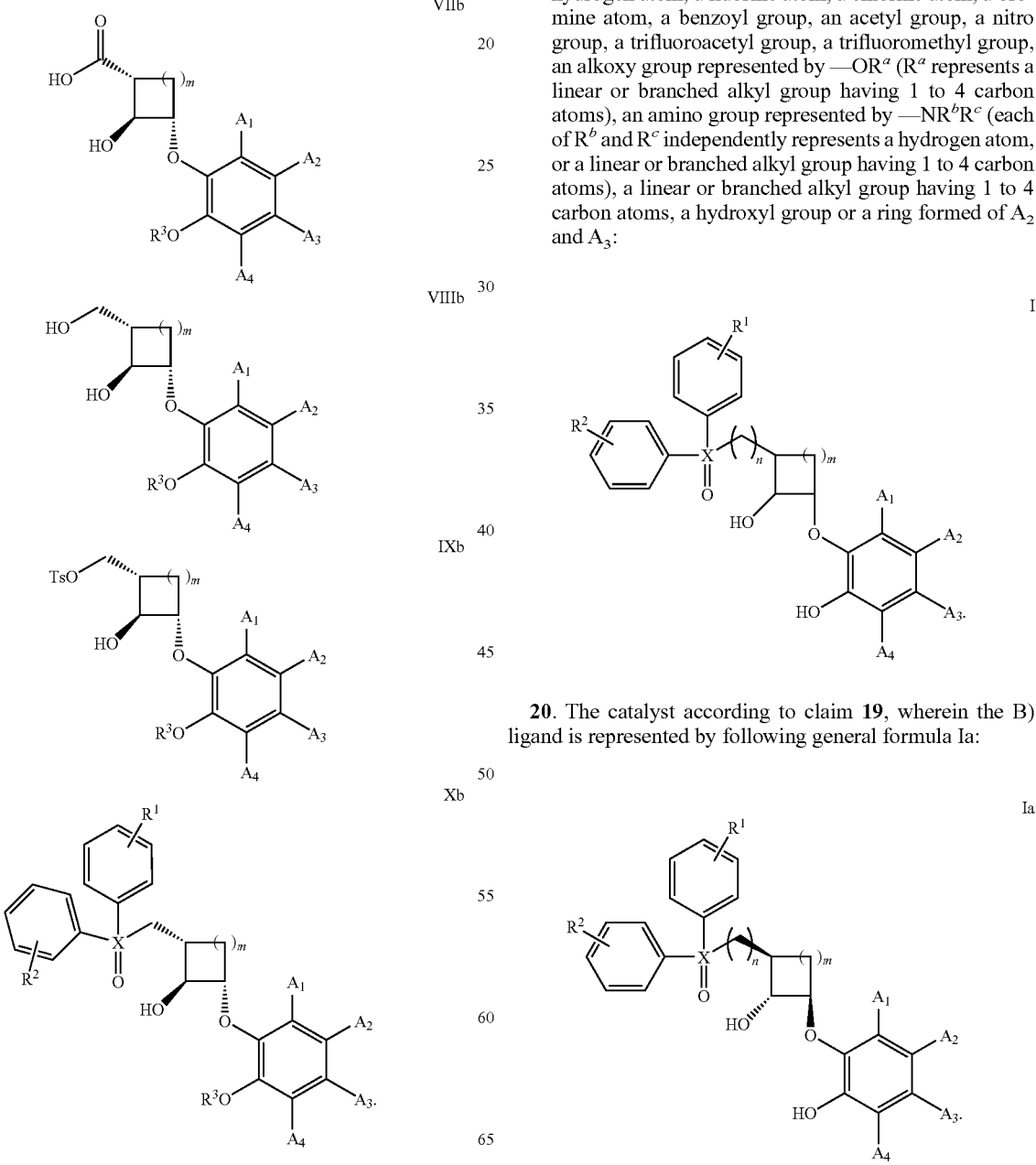

21. The catalyst according to claim 19, wherein the B) ligand is represented by following general formula Ib:

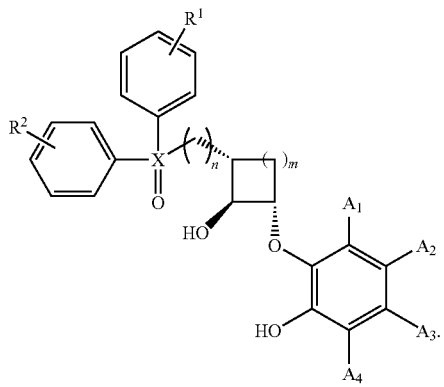

22. The catalyst according to claim 19, wherein the A) metal alkoxide or metal amide and B) ligand are 1:1 to 1:4 by molar ratio of A:B.

23. The catalyst according to claim 19, wherein the rare earth metal is ytterbium, yttrium, lanthanum, cerium, praseodymium, samarium, europium, gadolinium, dysprosium, holmium or erbium.

24. The catalyst according to claim 19, wherein alkyl of the trialkylsilyl group is a linear or branched alkyl having 1 to 4 carbon atoms.

25. The catalyst according to claim 19, wherein a metal alkoxide or metal amide of the A) is gadolinium triisopropoxide, yttrium triisopropoxide, tris-[N,N-bis(trimethylsilyl)amide]gadolinium (III), tris-[N,N-bis(trimethylsilyl)amide]yttrium (III) or barium diisopropoxide.

26. The catalyst according to claim 19, wherein the m is an integer of 2 to 4.

27. The catalyst according to claim 19, wherein two of the A1 to A4 are hydrogen atoms and the other two are fluorine atoms.

28. The catalyst according to claim 19, wherein the n is an integer of 0 or 1.

* * * * *

UNITED STATES PATENT AND TRADEMARK OFFICE
CERTIFICATE OF CORRECTION

| | |
|---|---|
| PATENT NO. | : 7,820,862 B2 |
| APPLICATION NO. | : 12/281361 |
| DATED | : October 26, 2010 |
| INVENTOR(S) | : M. Shibasaki et al. |

It is certified that error appears in the above-identified patent and that said Letters Patent is hereby corrected as shown below:

| COLUMN | LINE | ERROR |
|---|---|---|
| 42 (Claim 10, | 51 line 5 of text) | "in represents" should read --m represents-- |
| 43 (Claim 11, | 39 line 4 of text) | "wherein in has" should read --wherein m has-- |
| 48 (Claim 17, | 52 line 23 of text) | "in has the same definition" should read --m has the same definition-- |
| 48 (Claim 17, | 64 line 35 of text) | "dimethyl sulfide" should read --dimethylsulfide-- |

Signed and Sealed this
Fifteenth Day of March, 2011

David J. Kappos
*Director of the United States Patent and Trademark Office*